(12) United States Patent
Drouot et al.

(10) Patent No.: US 9,115,059 B2
(45) Date of Patent: Aug. 25, 2015

(54) OXIME DERIVATIVES OF 3,5-SECO-4-NOR-CHOLESTANE, PHARMACEUTICAL COMPOSITIONS CONTAINING SAME, AND METHOD FOR PREPARING SAME

(75) Inventors: Cyrille Drouot, Draguignan (FR); Abdesslame Nazih, Marseilles (FR); Corinne Chaimbault, Marseilles (FR)

(73) Assignee: TROPHOS, Marseilles (FR)

( * ) Notice: Subject to any disclaimer, the term of this patent is extended or adjusted under 35 U.S.C. 154(b) by 712 days.

(21) Appl. No.: 13/142,534

(22) PCT Filed: Dec. 17, 2009

(86) PCT No.: PCT/FR2009/001434
§ 371 (c)(1),
(2), (4) Date: Jun. 28, 2011

(87) PCT Pub. No.: WO2010/076418
PCT Pub. Date: Jul. 8, 2010

(65) Prior Publication Data
US 2011/0275680 A1    Nov. 10, 2011

(30) Foreign Application Priority Data
Dec. 29, 2008  (FR) ........................................ 08 07476

(51) Int. Cl.
C07C 251/44  (2006.01)
C07D 271/08  (2006.01)
C07D 495/04  (2006.01)

(52) U.S. Cl.
CPC ............ *C07C 251/44* (2013.01); *C07D 271/08* (2013.01); *C07D 495/04* (2013.01); *C07C 2103/16* (2013.01)

(58) Field of Classification Search
CPC   C07C 251/44; C07C 2103/16; C07D 271/08; C07D 495/04
See application file for complete search history.

(56) References Cited

U.S. PATENT DOCUMENTS 4,732,897 A * 3/1988 Cainelli et al. ............. 514/228.2
7,985,774 B2 * 7/2011 Pruss et al. .................... 514/640
8,338,488 B2 * 12/2012 Pruss et al. .................... 514/640
2008/0275130 A1 * 11/2008 Bordet et al. .................. 514/640
2009/0312434 A1    12/2009 Pruss et al.

FOREIGN PATENT DOCUMENTS

| EP | 0200859 A | 11/1986 |
| WO | WO 2008056059 A2 | 5/2005 |
| WO | WO 2006027454 A | 3/2006 |
| WO | WO 2006027454 A1 * | 3/2006 |
| WO | WO 2007101925 A1 | 9/2007 |

OTHER PUBLICATIONS

Rodewald, et al., "Aza-steroid Alkaloids. Synthesis of A-Nor-B-homo-5-azacholestane", Bulletin De L'Academie Polonaise Des Sciences Serie des sciences chimiques, May 30, 1963, pp. 437-441, vol. 11, No. 8.
Turner, "Steroids labeled with isotopic carbon: Cholestenone and testosterone", Journal of the American Chemical Society, 1950, p. 1, vol. 72.
Shoppee, et al., "Aza steroids. IV. 3-aza-5.alpha.- and -5.beta.-cholestane, 4-aza-5.alpha.a- and -5.beta.-cholestane, and related compounds", Journal of the Chemical Society, 1962, p. 1.
Castells, et al., "Steroids of natural configuration. I. Stereochemistry of lumisterol and 9.alpha.-lumisterol (pyrocalciferol)", Journal of the Chemical Society, 1959, p. 1.
Pradhan, et al., "A novel reductive cyclization involving attack by an oxime on an unconjugated alkyne. A new route to 4-aza sterols", Tetrahedron Letters, 1983, pp. 1-2, vol. 24, No. 45.
Ahmad, et al., "Azasteroids for methyl-5-oxo-4, 5-secocholestan-4-oate and related compounds", Indian Journal of Chemistry, Section B: Organic Chemistry Including Medicinal Chemistry, 1977, p. 1, vol. 15B, No. 12.
Barton, et al., "Photochemical transformations. XXVII. New partial synthesis of 4-demethyl and 4-bisdemethyl triterpenoids. The synthesis of 4.alpha., 14-dimethylzymosterol acetate", Justus Liebigs Annalen der Chemie, 1970, p. 1, vol. 737.

* cited by examiner

*Primary Examiner* — Matthew Coughlin
(74) *Attorney, Agent, or Firm* — Browdy and Neimark, PLLC

(57) ABSTRACT

The invention relates to novel chemical compounds, in particular oxime derivatives of 3,5-seco-4-nor-cholestane, to the application thereof as drugs, in particular cytoprotective drugs, and more particularly as neuroprotective, cardioprotective and/or hepatoprotective drugs.

7 Claims, No Drawings

OXIME DERIVATIVES OF 3,5-SECO-4-NOR-CHOLESTANE, PHARMACEUTICAL COMPOSITIONS CONTAINING SAME, AND METHOD FOR PREPARING SAME

The present invention relates to novel chemical compounds, particularly oxime derivatives of 3,5-seco-4-nor-cholestane, and application thereof as medicaments, in particular as cytoprotective medicaments, particularly as neuroprotective, cardioprotective and/or hepatoprotective medicaments.

Said medicaments are particularly suitable for pathologies and injuries associated with the degeneration or death of cells, particularly of motoneurons and/or cardiomyocytes and/or hepatocytes.

The invention also relates to pharmaceutical compositions containing said compounds, and the method of preparing them.

Cellular degenerative processes are characterized by dysfunction of the cells, often leading to undesirable cellular activities and cell death.

Cells have developed mechanisms for adaptation, in response to stress, which prolong their life or delay or prevent cell death (cytoprotective mechanisms).

However, these cytoprotective mechanisms are sometimes insufficient, inadequate, or induced too late to be effective and the cells die. It may therefore prove beneficial to have at our disposal new, cytoprotective, medicaments that would promote cytoprotection.

The principal mechanisms of cell death are divided essentially into necrosis, apoptosis and necroptosis.

Necrosis is so-called "accidental" cell death which occurs during tissue damage. It is the plasma membrane of the cell that is most affected, leading to a change in homeostasis of the cell. The cells will take in water to the point that this leads to lysis of their plasma membrane. This cellular lysis leads to release of the cytoplasmic contents into the surroundings. Necrosis is at the origin of the inflammatory process.

Necrosis can affect a group of cells or a tissue while other parts in the vicinity remain alive. The resulting transformation is a mortification of the cells or of the tissues.

In other words, necrosis is defined by morphological changes occurring when a cell comes to the end of its life following events such as a significant injury, such as an interruption or decrease in blood circulation in an organ, hyperthermia (large temperature rise), intoxication with a chemical, physical shock, etc.

One of the best known necroses is that of the myocardium during infarction (interruption of blood supply to the heart muscle) due to an occlusion (obstruction) of a coronary artery.

Apoptosis is an integral part of the normal physiology of an organism. It is a physiological form of highly regulated cell death and it is necessary for the survival of multicellular organisms. Apoptosis is a process that plays a crucial role during embryogenesis.

Cells that are in apoptosis, or are apoptotic, will isolate themselves from other cells. Apoptosis usually involves individual cells in a tissue and does not cause inflammation. One of the morphological characteristics of apoptosis is considerable condensation both of the nucleus and of the cytoplasm, resulting in a significant decrease in cell volume. The nucleus then undergoes fragmentation, and each fragment is surrounded by a double envelope. Apoptotic bodies (cytoplasmic and nuclear elements) are then released and will be absorbed by nearby cells by phagocytosis.

Apoptosis can be induced in various ways. For example, radiation, the presence of a chemical compound or of a hormone are stimuli that may induce a cascade of apoptotic events in the cell. Intracellular signals such as incomplete mitosis or damage to the DNA can also induce apoptosis.

Apoptosis also occurs after the action of a genotoxic agent or in the course of a disease. Certain pathologies are characterized by abnormal apoptosis, leading to loss of certain cellular populations, such as for example hepatotoxicity, retinopathies, and cardiotoxicity.

A distinction is therefore made between physiological apoptosis and pathological apoptosis. The invention relates, advantageously, to pathological apoptosis.

There are other mechanisms of cell death, for example necroptosis, which displays characteristics of necrosis and of apoptosis. A cell that is dying by necroptosis displays characteristics similar to those of a cell dying by necrosis, but the biochemical stages of this mechanism are more like those of apoptosis. This mechanism of cell death is involved for example in ischaemia.

It is therefore also one of the aims of the present invention to provide new medicaments that would make it possible to prevent and/or treat necrosis and/or pathological apoptosis and/or necroptosis (antinecrotic and/or antiapoptotic and/or antinecroptotic medicaments).

Cellular degenerative processes can result from, among other things, pathological situations grouped under the term of degenerative diseases or disorders, injuries, or exposure to various factors.

These injuries and factors can include, for example, exposure to radiation (UV, gamma), hypoxia or oxygen deprivation, deprivation of nutrients, deprivation of growth factors, poisons, cellular toxins, wastes, environmental toxins, free radicals, reactive oxygens. We may also mention chemical or biological agents used as therapeutic agents in the context of medical treatments, for example cytostatic agents or anti-inflammatory agents. Ischaemia-reperfusion phenomena may also be mentioned.

The most important pathological situations characterized by a degenerative process include:
  diseases of the bones, joints, connective tissue and cartilage, such as osteoporosis, osteomyelitis, arthritis including for example osteoarthritis, rheumatoid arthritis and psoriatic arthritis, avascular necrosis, fibrodysplasia ossificans progressiva, rickets, Cushing's syndrome;
  muscular diseases such as muscular dystrophy, for example Duchenne muscular dystrophy, myotonic dystrophies, myopathies and myasthenias;
  skin diseases, such as dermatitis, eczema, psoriasis, ageing, or impaired healing;
  cardiovascular diseases such as cardiac and/or vascular ischaemia, myocardial infarction, ischaemic cardiopathy, chronic or acute heart failure, cardiac dysrhythmia, atrial fibrillation, ventricular fibrillation, paroxysmal tachycardia, heart failure, hypertrophic cardiomyopathy, anoxia, hypoxia, side effects due to therapy with anticancer agents, cardiac lesions associated with reperfusion following ischaemia, either accidental or induced (surgical intervention);
  circulatory diseases such as atherosclerosis, arterial scleroses, peripheral vascular diseases, cerebrovascular accidents, aneurysms;
  haematological and vascular diseases such as: anaemia, vascular amyloidosis, haemorrhages, drepanocytosis, red cell fragmentation syndrome, neutropenia, leukopenia, bone marrow aplasia, pancytopenia, thrombocytopenia, haemophilia;

lung diseases including pneumonia, asthma; chronic obstructive pulmonary diseases, for example chronic bronchitis and emphysema;

diseases of the gastrointestinal tract, such as ulcers; diseases of the liver, for example hepatitis and in particular hepatitis of viral origin or having other infectious agents as the causative agent, alcoholic hepatitis, autoimmune hepatitis, fulminant hepatitis, certain hereditary metabolic disorders, Wilson's disease, cirrhoses, alcoholic liver disease (ALD), liver diseases due to toxins or medication; steatoses, for example:

non-alcoholic steatohepatitis (NASH), or that accompanying exogenous intoxication with alcohol or medicaments, viral or toxic hepatitis, complications of surgical procedures, metabolic diseases (such as diabetes, glucose intolerance syndrome, obesity, hyperlipidaemias, dysfunctions of the hypothalamo-hypophyseal axis, abetalipoproteinaemia, galactosaemias, glycogen diseases, Wilson's disease, Weber-Christian disease, Refsum syndrome, carnitine deficiency), hepatic complications of inflammatory diseases of the alimentary canal, autoimmune hepatitis.

Through action on steatosis or action on hepatic apoptosis, whatever its cause, the compounds could have a preventive action on the development of hepatic fibrosis and prevention of the occurrence of cirrhoses.

diseases of the pancreas, for example acute or chronic pancreatitis;

metabolic diseases such as diabetes mellitus and diabetes insipidus, thyroiditis;

kidney diseases, for example acute renal disorders or glomerulonephritis;

viral and bacterial infections such as septicaemia;

severe intoxications with chemicals, toxins or drugs;

degenerative disorders associated with acquired immunodeficiency syndrome (AIDS);

disorders associated with ageing, such as accelerated ageing syndrome;

inflammatory diseases, such as Crohn's disease, rheumatoid arthritis;

autoimmune diseases such as lupus erythematosus;

dental disorders such as those resulting in tissue degradation, for example periodontitis;

ophthalmic diseases or disorders including diabetic retinopathies, glaucoma, macular degeneration, retinal degeneration, retinitis pigmentosa, holes or tears in the retina, detachment of the retina, retinal ischaemia, acute retinopathies associated with an injury, inflammatory degeneration, postoperative complications, medicament-induced retinopathies, cataract;

disorders of the auditory tract, such as otosclerosis and antibiotic-induced deafness;

diseases associated with the mitochondria (mitochondrial pathologies), such as Friedreich's ataxia, congenital muscular dystrophy with mitochondrial structural abnormalities, certain myopathies (MELAS syndrome, MERFF syndrome, Pearson syndrome), MIDD syndrome (maternally inherited diabetes and deafness), Wolfram syndrome, dystonia.

Moreover, the neurodegenerative processes are characterized by dysfunction and death of neurons leading to loss of neurological functions mediated by the brain (central nervous system, CNS), spinal cord and peripheral nervous system (PNS). They can result inter alia from pathological situations under the heading neurodegenerative diseases or disorders, from injury, or from exposure to toxins.

The most important pathologies that are characterized by a neurodegenerative process are:

chronic neurodegenerative diseases, in particular chronic demyelinating diseases, hereditary or sporadic, advantageously Alzheimer's disease, Huntington's disease, Parkinson's disease, amyotrophic lateral sclerosis, spinal muscular atrophy, especially infantile, Creutzfeldt-Jacob disease, multiple sclerosis, amyotrophic lateral scleroses, leukodystrophies including adrenoleukodystrophy, epilepsy, dementias, schizophrenia, and neurological syndromes associated with AIDS;

neuronal lesions connected with ageing;

hereditary or lesion-induced peripheral neuropathies, such as Fabry disease, Charcot-Marie-Tooth disease, Krabbe disease, leukodystrophies, diabetic neuropathies and those induced by anti-cancer treatments;

injuries of the brain, of the peripheral nerves or of the spinal cord;

ischaemias of the brain or of the spinal cord following a cerebrovascular accident, or induced by a lack of blood supply;

hereditary, lesion-induced or age-related degeneration of the sensory neurons of vision, such as macular degeneration, retinitis pigmentosa, or glaucoma-induced degeneration of the optic nerve;

hereditary, traumatic or age-related degeneration of the sensory neurons of hearing leading to hearing impairment or loss.

Some of the signalling pathways affected in these pathologies are common to a large number of neurodegenerative diseases. Alzheimer's disease is the commonest dementia. It leads to atrophy of the brain, neuronal loss predominantly in the cornu ammonis and it also affects the cholinergic neurons. Other pathologies, such as lobar atrophies (Pick's disease, Creutzfeld-Jacob disease), dementia with Lewy bodies, vascular dementias, and Parkinson's disease are associated with considerable neuronal death which accounts for the symptoms of these dementias.

One therapeutic approach for protecting neurons against death is to supply neurotrophic proteins.

These proteins, such as BDNF (brain-derived neurotrophic factor), CNTF (ciliary neurotrophic factor), NGF (nerve growth factor), GDNF (glia-derived neurotrophic factor), are synthesized during embryonic development or after injury in the adult. These growth factors promote the survival, maturation and differentiation of nerve cells. Moreover, they inhibit the apoptotic mechanisms, activate multiple survival pathways and protect a large number of neuronal populations. Their use is proposed in most forms of neuronal degeneration.

Compounds that would activate the expression of neurotrophic factors or would mimic the action of these factors have a therapeutic potential for the treatment of neurodegenerative syndromes.

In particular, supply of neurotrophic molecules for the treatment of neuronal degeneration has three objectives:

to compensate a potential deficiency of neurotrophic factors linked to lack of supply by the peripheral or central targets of the neurons and/or a disorder of reverse transport of these factors;

to intervene non-specifically in the biochemical pathways involved in the degenerative cascade;

to promote the natural compensatory phenomena of dendritic growth and arborization of the nerve endings.

These compounds would therefore have a beneficial effect in a large number of pathologies and in particular in pathologies affecting the peripheral and central nervous systems.

Moreover, the motoneurons are neurons that are in particular present in the spinal cord and brainstem. Their degeneration or their death can lead to a progressive weakening of the muscles of the limbs, then to atrophy and possibly to spasticity (i.e. permanent contraction) of the muscles.

The most important pathologies resulting from degeneration and death of spinal and/or bulbar motoneurons are amyotrophic lateral sclerosis, also known as Charcot's disease or Lou Gehrig disease, and spinal muscular atrophy, particularly infantile, also known as Werdnig-Hoffmann disease or Kugelberg-Welander disease.

Moreover, degeneration of motoneurons is observed in cases of injuries with crushing and/or severing of the spinal cord or of the peripheral motor nerves.

More generally, the term spinal muscular atrophy is used for diseases where degeneration or death of the motoneurons of the spinal cord is implicated.

Amyotrophic lateral sclerosis (ALS) is a neurodegenerative disease associated with different types of inclusions such as Lewis bodies and is characterized by degeneration of spinal and cortical motoneurons, in which a fatal outcome is sometimes associated with frontal lobe dementia. In the course of development of ALS, degenerative phenomena occur not only in the brain but also in the spinal cord and consequently in the muscles, through lack of innervation.

Regarding chemical structures, the literature provides some examples of oxime derivatives of 3,5-seco-4-nor-cholestane. These derivatives are generally described as synthesis intermediates, in particular for the synthesis of azasteroids. Oxime derivatives of 3,5-seco-4-nor-cholestane possessing neuroprotective or cytoprotective properties are described in patent applications WO2006/027454 (A1) and WO2007/101925 (A1) respectively.

However, without denigrating the currently known treatments, to date there is no pharmacological treatment that is really effective for treating the cytodegenerative diseases that are characterized by cellular dysfunction and death, and in particular for treating neurodegenerative diseases. Thus, there is still a real need for new products providing effective protection of the cells against the phenomena of degeneration.

The compounds of the present invention, besides being novel, display very interesting pharmacological properties.

They are found advantageously to be cytoprotective, and in particular neuroprotective and/or cardioprotective and/or hepatoprotective.

In addition to their biological activity, some of these novel compounds may also display advantageous properties in relation to their pharmacological activity, such as their pharmacokinetics, their bioavailability, their solubility, their stability, their toxicity, their absorption and/or their metabolism. This makes them very useful for preparing a medicament, in particular for preparing a medicament that is cytoprotective, and very particularly neuroprotective and/or cardioprotective and/or hepatoprotective.

More specifically, the present invention relates to novel compounds corresponding to formula (I):

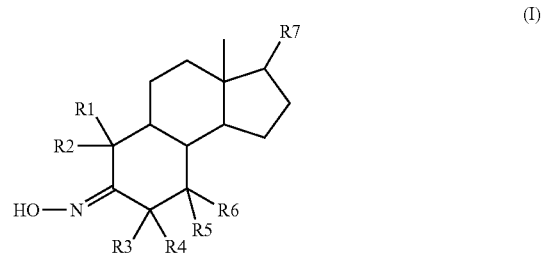

in which,
$R_1$ can represent a hydrogen atom or a —$CH_3$, —$CH_2$—CN, —$CH_2$—$OR^a$, —$CH_2$—$SR^a$, —$CH_2$—$SeR^a$, —C(O)$OR^a$, —O—C(O)$NR^aR^b$, —C(O)$NR^aR^b$ group in which,
(i) $R^a$ and $R^b$, simultaneously or independently of one another, can be selected from a hydrogen atom or a $C_1$-$C_6$ alkyl, $C_3$-$C_6$ cycloalkyl, aryl, heteroaryl group or
(ii) $R^a$ and $R^b$, taken together with the nitrogen to which they are attached, can form a non-aromatic $C_3$-$C_6$ heterocycle, and said heterocycle can have one or more double bonds and/or one or more atom(s) of oxygen, of sulphur or of nitrogen;
$R_2$ can represent a hydrogen atom or a $C_1$-$C_8$ alkyl, $C_2$-$C_8$ alkenyl, $C_2$-$C_8$ alkynyl group, or a halogen atom or a group corresponding to formula (A):

in which
(i) n can represent an integer that can take any one of the values from 1 to 8; and
(ii) Q can represent an oxygen atom or an —$NR^a$ group in which $R^a$ is as defined previously and $R^c$ can represent a hydrogen atom or a $C_1$-$C_6$ alkyl, aryl, heteroaryl group, a heterocycle, $C_1$-$C_6$ alkyl-C(O)—, aryl-C(O)—, heteroaryl-C(O)—, heterocycle-C(O)—, in particular a group represented by one of the formulae (C) or (D)

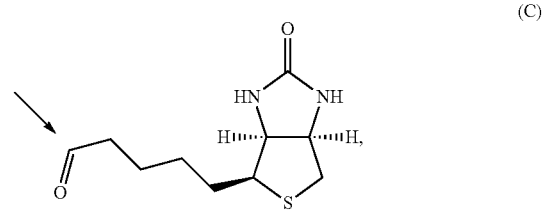

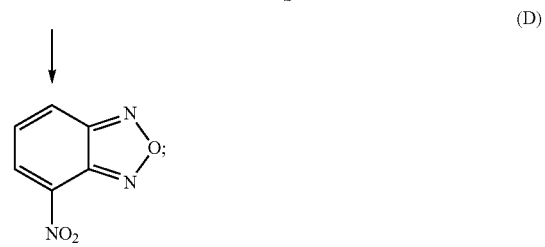

or
(iii) Q can represent an —O—C(O)— group or an —$NR^a$—C(O)— group in which $R^a$ is as defined previously and $R^c$ can represent a hydrogen atom or a $C_1$-$C_6$ alkyl, aryl, heteroaryl group, a heterocycle, $R_3$ can represent a hydrogen atom or a $C_1$-$C_6$ alkyl, $C_3$-$C_6$ cycloalkyl, $C_2$-$C_6$ alkenyl, $C_2$-$C_6$ alkynyl, aryl group, a heterocycle, or a halogen atom or a —CN, —CF$_3$, —NO$_2$, —OR$^a$, —SR$^a$, —SO$_2$R$^a$, —NR$^a$R$^b$, —OC(O)R$^a$, —OC(O)NR$^a$R$^b$, —C(O)OR$^a$, —CONR$^a$R$^b$ group, $R^a$ and $R^b$ can be as defined previously;

$R_4$ can represent a hydrogen atom or a $C_1$-$C_6$ alkyl group, or $R_3$ and $R_4$ taken together with the carbon to which they are attached, can form a ($C_3$-$C_6$)-cycloalkyl group;

$R_5$ can represent a hydrogen atom or a $C_1$-$C_6$ alkyl group, preferably a hydrogen atom or a hydroxyamino (—NH$_2$—OH) group or $R_4$ and $R_5$ taken together can form an additional carbon-carbon bond between the carbon atoms to which they are attached, or a $C_3$-$C_6$ cycloalkyl group;

$R_6$ can represent a hydrogen atom or a $C_1$-$C_6$ alkyl, $C_3$-$C_6$ cycloalkyl, $C_2$-$C_6$ alkenyl, $C_2$-$C_6$ alkynyl, aryl group, or a —CN, —OR$^a$, —SR$^a$, —SO$_2$R$^a$, —NR$^a$R$^b$, —OC(O)R$^a$, —OC(O)NR$^a$R$^b$ group, $R^a$ and $R^b$ can be as defined previously, or a hydroxyamino (—NH$_2$—OH) group;

$R_7$ can represent a $C_4$-$C_{12}$ alkyl group, $C_4$-$C_{12}$ alkenyl group or a $C_4$-$C_{12}$ alkynyl group, in particular a group selected from

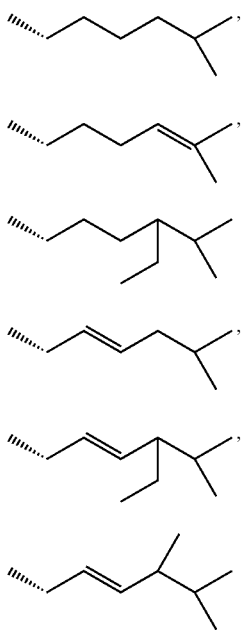

as well as:
its SYN, ANTI isomers, when they exist,
its optical isomers (enantiomers, diastereoisomers), when they exist,
its addition salts with a pharmaceutically acceptable acid or base,
its hydrates and its solvates,
its prodrugs,
with the exception of the following compounds:
the ester of 4-nor-3,5-secocholestan-5-one oxime-3-N,N-dimethylglycine;
the ester hydrochloride of 4-nor-3,5-secocholestan-5-one oxime-3-N,N-dimethylglycine;
4-nor-3,5-secocholestan-3-ol-5-one oxime;
4-nor-3,5-secocholestan-3,5-dione dioxime;
4-nor-3,5-secocholestan-5-one oxime-3-(4-methyl-1-piperazine)-propanoic ester;
3-aminomethyl-4-nor-3,5-secocholestan-5-one oxime;
4,5-secocholestan-3-ol-5-one oxime;
3-methyl-4,5-secocholestan-3-ol-5-one oxime;
3-N-methylcarboxamide-4-nor-3,5-secocholestan-5-one oxime;
5-hydroxyimino-4-nor-3,5-secocholestan-3-oic acid;
3,4-nor-2,5-secocholestan-5-one oxime;
methyl 5-hydroxyimino-4-nor-3,5-secostigmastan-3-oate;
methyl 5-hydroxyimino-4-nor-3,5-secocholestan-3-oate;
4,5-secocholestan-3,5-dione dioxime;
4,5-secocholestan-3-yn-5-one oxime;
24-methyl-A-nor-1,5-secocholest-21-en-5-one oxime;
3-(O-methyloxime)-4,5-secocholestan-3,5-dione 5-oxime;
4-methylidyne-4,5-secocholestan-5-one oxime;
4-methyl-4,5-secocholestan-3-yn-5-one oxime;
methyl 5-hydroxyimino-4,5-secocholestan-4-oate;
5-hydroxyimino-4,5-secocholestan-4-oic acid;
3-oxo-4,5-secocholestan-5-one oxime;
3-acetyloxy-4-nor-3,5-secocholestan-5-one oxime;
4,5-secocholestan-4-ol-5-one oxime;
3-hydroxymethyl-4,5-secocholestan-4-ol-5-one oxime;
24-N,N-diethylcarbamoyl-3,5-seco-4-norcholane-5-hydroxyimino-3-oic acid.

According to the present text,
the term "$C_x$-$C_y$ alkyl" refers to a linear or branched hydrocarbon radical, comprising from x to y carbon atoms. Thus, by way of examples, depending on the cases listed, the invention covers linear or branched hydrocarbon radicals, such as methyl, ethyl, propyl, isopropyl, butyl, isobutyl, tert-butyl, pentyl, neopentyl, n-hexyl, n-heptyl, n-octyl, n-nonyl, n-decyl, n-undecyl, n-dodecyl. The $C_1$-$C_6$ alkyl groups are preferred. The alkyl groups can optionally be substituted with an aryl group as defined below, in which case it is called an arylalkyl group. Examples of arylalkyl groups are in particular benzyl and phenethyl. Optionally, the alkyl groups can be substituted one or more times with one of the substituents selected independently from a halogen atom or a —CN, —CF$_3$, —COOR$^a$, —CONR$^a$R$^b$, —O—CONR$^a$R$^b$, —NR$^a$R$^b$, —OR$^a$, —SR$^b$ group, where the $R^a$ and $R^b$ groups can be as described previously.

the term "$C_x$-$C_y$ alkenyl" refers to a linear or branched or cyclic hydrocarbon radical, comprising one or more double bonds, having from x to y carbon atoms. There may be mentioned, for example, the ethenyl, 1-propenyl, 2-propenyl, 1-butenyl, 2-butenyl, 1-pentenyl, 2-pentenyl, 3-methyl-3-butenyl, 1-hexenyl, 1-hepted, 1-octenyl radical. Optionally, the alkenyl groups can be substituted one or more times with one of the substituents selected independently from a halogen atom or a —CN, —CF$_3$, —COOR$^a$, —C(O)NR$^a$R$^b$, —O—C(O)NR$^a$R$^b$, —NR$^a$R$^b$, —OR$^a$, —SR$^b$ group, where the $R^a$, $R^b$ groups can be as described previously;

the term "$C_x$-$C_y$ cycloalkyl" refers to a saturated or partially unsaturated cyclic hydrocarbon radical, having from x to y carbon atoms. The cycloalkyl groups in particular include the cyclopropyl, cyclobutyl, cyclopentyl, cyclopentenyl, cyclohexyl, cyclohexenyl substituents. Optionally, the cycloalkyl groups can be substituted one or more times with one of the substituents selected independently from a halogen atom or a —CN, —$CF_3$, —$COOR^a$, —$C(O)NR^aR^b$, —O—$C(O)NR^aR^b$, —$NR^aR^b$, —$OR^a$, —$SR^a$ group, the $R^a$, $R^b$ group can be as described previously;

the term "$C_x$-$C_y$ alkynyl" refers to a linear or branched hydrocarbon radical comprising at least one triple bond, having from x to y carbon atoms. The alkynyl groups in particular include the ethynyl, 1-propynyl, 2-propynyl, 1-butynyl, 2-butynyl, 1-pentynyl, 2-pentynyl, 1-heptynyl, 2-heptynyl, 1-octynyl, 2-octynyl substituents. Optionally, the alkynyl groups can be substituted one or more times with one of the substituents selected independently from a halogen atom or a —CN, —$CF_3$, —$COOR^a$, —$C(O)NR^aR^b$, —O—$C(O)NR^aR^b$, —$NR^aR^b$, —$OR^a$, —$SR^a$ group, the $R^a$, $R^b$ groups can be as described previously;

the term "$C_x$-$C_y$ aryl" refers to an aromatic hydrocarbon radical, having from x to y carbon atoms. According to the invention, aromatic hydrocarbon radicals having 6 carbon atoms are preferred. The aryl groups in particular include the phenyl, naphthyl and biphenyl radicals. Optionally, the aryl groups can be substituted one or more times with one of the substituents selected independently from a halogen atom or an alkyl, —CN, —$CF_3$, —$N_3$, —$NO_2$, —$COOR^a$, —$C(O)NR^aR^b$, —O—$C(O)NR^aR^b$, —$NR^aR^b$, —$OR^a$, —$SR^a$ group, the $R^a$, $R^b$ groups can be as described previously;

the term "$C_x$-$C_y$ heterocycle" refers to a saturated, unsaturated or aromatic mono- or polycyclic radical, optionally substituted, which can have from x to y carbon atoms and comprises one or more heteroatoms. Preferably, the heteroatoms are selected from oxygen, sulphur and nitrogen. Examples of heterocycle are the furyl, thienyl, pyrrole, imidazole, isothiazole, thiazole, isoxazole, oxazole, pyridine, pyrazine, pyrimidine, pyridazine, indole, isoindole, indazole, quinoline, isoquinoline, phthalazine, quinazoline, pyrrolidine, imidazolidine, pyrrazolidine, piperidine, piperazine, morpholine, thiazolidine, phthalimide or benzimidazole radicals. Optionally, the heterocyclic groups can be substituted one or more times with one of the substituents selected independently from a halogen atom or an alkyl, —CN, —$CF_3$, —$N_3$, —$NO_2$, —$COOR^a$, —$C(O)NR^aR^b$, —O—$C(O)NR^aR^b$, —$NR^aR^b$, —$OR^a$, —$SR^a$ group, the $R^a$, $R^b$ groups can be as described previously;

the term "halogen" refers to a chlorine, bromine, fluorine and iodine atom. Preferably according to the invention, the halogen will be a fluorine atom;

the term "treatment" denotes preventive, curative, palliative treatment, as well as patient management (reduction of suffering, prolongation of life, slowing of disease progression), etc. The treatment can moreover be carried out in combination with other ingredients or treatments, such as in particular other active compounds for treating the pathologies or injuries specified in the present application;

the term "cytoprotective" refers to the capacity of agents, for example natural or synthetic chemical compounds, to maintain the interactions of cells with one another or with other tissues, to protect cells against degenerative phenomena leading to a loss of cellular function or to undesirable cellular activities, with or without cell death, and/or against cellular dysfunction and/or against degenerative diseases or disorders leading to these cellular dysfunctions, said dysfunction or said diseases or disorders leading or not to cell death;

the terms "neuroprotective" or "cardioprotective" or "hepatoprotective" refer to the same properties of said agents but specifically for the cells of the nervous system ("neuroprotective") or specifically for the cells of the cardiac system ("cardioprotective"), or specifically for the cells of the hepatic system ("hepatoprotective"). It is therefore to be understood that a cytoprotective or neuroprotective or cardioprotective or hepatoprotective compound is a compound that has the properties described above.

Compounds of formula (I) that are particularly preferred are those in which, individually or in combination:

the substituent $R_1$ can be selected from a —$CH_3$ group and a —$CH_2$—OH group; preferably, the substituent $R_1$ can represent a —$CH_3$ group;

the substituent $R_2$ can be selected from a $C_1$-$C_8$ alkyl group, optionally a $C_1$-$C_4$ alkyl, —$CH_2$—$CH_2$—$CH_3$, —$CH_2$—$CH_2$—$CF_2$—$CH_3$, —$CH_2$—$CH_2$—CH(OH)—$CF_3$, —$CH_2$—CH(OH)—$CF_3$ and —$CH_2$—$CH_2$—OH group. Advantageously, the substituent $R_2$ can be selected from a —$CH_2$—$CH_2$—$CH_3$ and —$CH_2$—$CH_2$—OH group;

the substituent $R_3$ can be selected from a hydrogen atom, an alkyl group or a fluorine atom. Advantageously, the substituent $R_3$ can be selected from a hydrogen atom or a fluorine atom;

the substituents $R_4$, $R_5$ and $R_6$ can be hydrogen atoms;

when $R_4$ and $R_5$ taken together form an additional carbon-carbon bond between the carbon atoms to which they are attached, then the $R_3$ group represents a halogen atom, preferably a fluorine atom.

According to another aspect of the invention, the preferred substituent $R_2$ can represent a group corresponding to the following formula (A):

$R^c$-Q-$(CH_2)n$- \hfill (A)

in which n=3

Q can represent an —$NR^a$ group in which $R^a$ can represent a $CH_3$ group and $R^c$ can represent the group corresponding to formula (C)

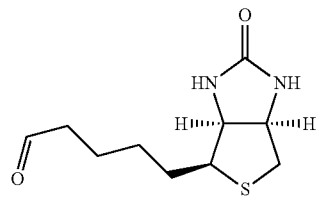

(C)

According to yet another aspect of the invention, other preferred compounds are those for which the substituent $R_2$ can represent a group corresponding to the following formula (A):

$R^c$-Q-$(CH_2)n$- \hfill (A)

in which n=3

Q can represent an $NR^a$ group, in which $R^a$ can represent a $CH_3$ group, and $R^c$ can represent a group selected from aryl, heteroaryl, heterocycle, in particular the group corresponding to the following formula (D):

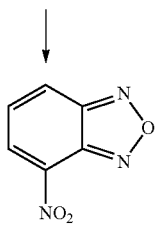
(D)

According to another aspect of the invention, the compounds for which $R_4$, together with $R_5$, forms an additional C—C bond between the carbon atoms to which $R_4$ and $R_5$ are attached, are also preferred.

Likewise, the compounds corresponding to formula (I) in which $R_6$ can represent an alkyl group, in particular a methyl or ethyl group are also preferred compounds.

The substituent $R_7$ that is particularly preferred according to the invention is selected from the following groups G1, G2 and G5:

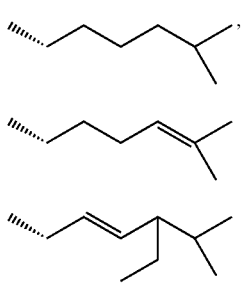

Particularly advantageously, the preferred compounds according to the present invention are:
4-nor-3,5-seco-3-(trifluoromethyl)cholestan-3-ol-5-one oxime;
3-[(N-(+)-biotinoyl-N-methyl)amino]-4-nor-3,5-secocholestan-5-one oxime;
3-[methyl(7-nitro-2,1,3-benzoxadiazol-4-yl)amino]-4-nor-3,5-secocholestan-5-one oxime;
25-fluoro-4-nor-3,5-secocholestan-3-ol-5-one oxime;
4-nor-3,5-secocholestan-5-one oxime;
3,4-dinor-2,5-secocholestan-2-ol-5-one oxime;
4-nor-3,5-secocholest-24-en-3-ol-5-one oxime,
24β-ethyl-4-nor-3,5-secocholest-22-en-3-ol-5-one oxime
as well as:
their SYN, ANTI isomers, when they exist,
their optical isomers (enantiomers, diastereoisomers), when they exist,
their addition salts with a pharmaceutically acceptable acid or base,
their hydrates and their solvates,
their prodrugs.

The addition salts with pharmaceutically acceptable acids can be for example salts formed with hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonic acids such as methane or ethane sulphonic, arylsulphonic acids, such as benzene or paratoluene sulphonic acids, or carboxylic acids.

Certain preferred compounds of the present invention possess one or more fluorine atoms. By way of example, 3,3-difluoro-3-methyl-4,5-secocholestan-5-one oxime and 4-nor-3,5-seco-3-(trifluoromethyl)cholestan-3-ol-5-one oxime are particularly preferred.

It should be noted that in the present text, the atom that can be represented by the general term "halogen" can also be a natural or synthetic radioactive isotope, for example for fluorine, fluorine-18 ($^{18}F$). The radiolabelled compounds of formula (I), particularly those labelled with the $^{18}F$ isotope, can be very useful for medical imaging, in particular for positron emission tomography (PET), which is an in vivo imaging technique developed for the diagnosis of diseases, for example in the field of oncology, neurology and cardiology. In the same line of thinking, there may be mentioned for bromine or iodine, the radiolabelled isotopes bromine-75 ($^{75}Br$) and iodine-124 ($^{124}I$) respectively.

The general term "halogen" can also cover, according to the present text, natural or synthetic non-radioactive isotopes, such as for example a non-radioactive isotope fluorine-19 ($^{19}F$), which is useful for biomedical research, and in particular in cognitive neurosciences and in particular for magnetic resonance imaging (MRI).

The compounds according to the present invention possess very interesting pharmacological properties. In particular they are endowed with remarkable cytoprotective, particularly neuroprotective properties, very particularly with respect to motoneurons, and cardioprotective and hepatoprotective properties.

These properties are illustrated below in the experimental section. They justify the use of the compounds described above as well as of their esters and/or of their addition salts with pharmaceutically acceptable acids, as cytoprotective medicaments, particularly neuroprotective and/or cardioprotective and/or hepatoprotective medicaments.

Quite particularly, the compounds according to the invention display remarkable activity with respect to motoneurons, neurons of the central nervous system, motor and peripheral nerves.

Thus, the invention also relates to the use, as a medicament, of compounds of formula (I), including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid as well as their esters, and/or their addition salts with pharmaceutically acceptable acids.

The invention therefore further relates to the use of a compound of formula (I), including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid as well as their esters, and/or their addition salts with pharmaceutically acceptable acids, for preparing a cytoprotective medicament.

The compounds according to the present invention can, on the basis of their cytoprotective properties, be used for preparing a medicament intended for the treatment or prevention of necrosis and/or pathological apoptosis and/or necroptosis (antinecrotic and/or antiapoptotic and/or antinecroptotic medicaments) or for the treatment or prevention of disorders such as:

- diseases of the bones, joints, connective tissue and cartilage, such as osteoporosis, osteomyelitis, arthritis including for example osteoarthritis, rheumatoid arthritis and psoriatic arthritis, avascular necrosis, fibrodysplasia ossificans progressiva, rickets, Cushing's syndrome;
- muscular diseases such as muscular dystrophy, for example Duchenne muscular dystrophy, myotonic dystrophies, myopathies and myasthenias;
- skin diseases, such as dermatitis, eczema, psoriasis, ageing, or impaired healing;
- cardiovascular diseases such as cardiac and/or vascular ischaemia, myocardial infarction, ischaemic cardiopathy, chronic or acute heart failure, cardiac dysrhythmia, atrial fibrillation, ventricular fibrillation, paroxysmal tachycardia, heart failure, hypertrophic cardiomyopathy, anoxia, hypoxia, side effects due to therapy with anticancer agents, cardiac lesions associated with reperfusion following accidental or induced (surgical intervention) ischaemia;
- circulatory diseases such as atherosclerosis, arterial scleroses, peripheral vascular diseases, cerebrovascular accidents, aneurysms;
- haematological and vascular diseases such as: anaemia, vascular amyloidosis, haemorrhages, drepanocytosis, red cell fragmentation syndrome, neutropenia, leukopenia, bone marrow aplasia, pancytopenia, thrombocytopenia, haemophilia;
- lung diseases including pneumonia, asthma; chronic obstructive pulmonary diseases for example chronic bronchitis and emphysema;
- diseases of the gastrointestinal tract, such as ulcers;
- diseases of the liver for example hepatitis particularly hepatitis of viral origin or having other infectious agents as the causative agent, alcoholic hepatitis, autoimmune hepatitis, fulminant hepatitis, certain hereditary metabolic disorders, Wilson's disease, cirrhoses, alcoholic liver disease (ALD), liver diseases due to toxins or medication; steatoses for example:
  - non-alcoholic steatohepatitis (NASH), or that accompanying exogenous intoxication with alcohol or drugs, viral or toxic hepatitis, complications of surgical procedures, metabolic diseases (such as diabetes, glucose intolerance syndrome, obesity, hyperlipidaemias, dysfunctions of the hypothalamic-hypophyseal axis, abetalipoproteinaemia, galactosaemias, glycogen diseases, Wilson's disease, Weber-Christian disease, Refsum syndrome, carnitine deficiency),
  - hepatic complications of inflammatory diseases of the alimentary canal,
  - autoimmune hepatitis.

Through action on steatosis or action on hepatic apoptosis, whatever its cause, the compounds could have a preventive effect on the development of hepatic fibrosis and prevention of occurrence of cirrhoses, and diseases of the pancreas for example acute or chronic pancreatitis;
- metabolic diseases such as diabetes mellitus and diabetes insipidus, thyroiditis;
- kidney diseases, for example acute renal disorders or glomerulonephritis;
- viral and bacterial infections such as septicaemia;
- severe intoxications with chemicals, toxins or drugs;
- degenerative disorders associated with acquired immunodeficiency syndrome (AIDS);
- disorders associated with ageing, such as accelerated ageing syndrome;
- inflammatory diseases, such as Crohn's disease, rheumatoid arthritis;
- autoimmune diseases such as lupus erythematosus;
- dental disorders such as those resulting in tissue degradation, for example periodontitis;
- ophthalmic diseases or disorders including diabetic retinopathies, glaucoma, macular degeneration, retinal degeneration, retinitis pigmentosa, holes or tears in the retina, detachment of the retina, retinal ischaemia, acute retinopathies associated with an injury, inflammatory degeneration, postoperative complications, drug-induced retinopathies, cataract;
- disorders of the auditory tract, such as otosclerosis and antibiotic-induced deafness;
- diseases associated with the mitochondria (mitochondrial pathologies), such as Friedreich's ataxia, congenital muscular dystrophy with mitochondrial structural abnormalities, certain myopathies (MELAS syndrome, MERFF syndrome, Pearson syndrome), MIDD syndrome (maternally inherited diabetes and deafness), Wolfram syndrome, dystonia.

Very particularly, the medicaments according to the present invention find application, on account of their neuroprotective properties, in the treatment or prevention of neurodegenerative disorders, for example Huntington's disease, chronic neurodegenerative diseases, advantageously chronic demyelinating neurodegenerative diseases, hereditary or sporadic, neuronal lesions connected with ageing, peripheral, hereditary or lesional neuropathies, diabetic neuropathies or those induced by anticancer treatments, injuries of the brain, of the peripheral nerves or of the spinal cord, ischaemias of the brain or of the spinal cord, epilepsy, degeneration that is hereditary, lesional or connected with ageing of the sensory neurons of vision or degeneration of the optic nerve, degeneration that is hereditary, traumatic or connected with ageing of the sensory neurons of hearing, lobar atrophies and vascular dementias, and in particular spinal muscular atrophy, amyotrophic lateral sclerosis and pathologies due to injuries of the spinal cord or of peripheral motor nerves.

On account of their neuroprotective properties with respect to motoneurons, they can be used in particular in the treatment of spinal muscular atrophy, in particular of amyotrophic lateral sclerosis or of infantile spinal muscular atrophies, and in the treatment of injuries of the spinal cord or of peripheral motor nerves as mentioned above.

In general the daily dose of the compound will be the minimum dose for obtaining the therapeutic effect. This dose will depend on the various factors already mentioned. The doses of the compounds described above including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid can in general be from 0.001 to 100 mg per kilogram per day for humans.

If necessary, the daily dose can be administered in two, three, four, five, six or more individual doses per day or by multiple sub-doses administered at suitable intervals throughout the day.

The quantity selected will depend on many factors, in particular the route of administration, the duration of administration, the moment of administration, the rate of elimination of the compound, of the product or various products used in combination with the compound, the patient's age, weight and physical condition as well as their medical history, and any other information known in medicine.

The prescription of the attending doctor can begin at doses lower than those generally used, then these doses will be increased gradually for better management of the development of any side effects.

The invention also relates to pharmaceutical compositions that comprise at least one compound of formula (I), including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid or one of its esters and/or of its addition salts with pharmaceutically acceptable acids, as active ingredient.

In these compositions, the active ingredient is advantageously present at physiologically effective doses; the aforementioned compositions can in particular comprise an effective neuroprotective dose of at least one active ingredient mentioned above.

As medicaments, the compounds corresponding to formula (I), including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid as well as their esters and/or their addition salts with pharmaceutically acceptable acids can be incorporated in pharmaceutical compositions intended for the gastrointestinal or parenteral route.

The pharmaceutical compositions according to the invention can further comprise at least one other therapeutically active ingredient. to be used simultaneously, separately or spread over time, in particular during a treatment in a subject affected by a pathology or an injury associated with degeneration or death of cells and particularly of cardiac cells and/or of motoneurons as defined above.

The pharmaceutical compositions or medicaments according to the invention advantageously comprise one or more inert excipients or vehicles, i.e. pharmaceutically inactive and non-toxic. There may be mentioned for example physiological, isotonic, buffered, etc. saline solutions, compatible with pharmaceutical use and known to a person skilled in the art. The compositions can contain one or more agents or vehicles selected from dispersants, solubilizing agents, stabilizers, preservatives, etc. Agents or vehicles usable in formulations (liquid and/or injectable and/or solid) are in particular methylcellulose, hydroxymethylcellulose, carboxymethylcellulose, cyclodextrins, polysorbate 80, mannitol, gelatin, lactose, vegetable or animal oils, gum arabic, etc. The compositions can be formulated in the form of injectable suspension, gels, oils, tablets, suppositories, powders, soft capsules, hard capsules, etc., optionally by means of pharmaceutical forms or devices providing sustained and/or delayed release. For this type of formulation, an agent such as cellulose, carbonates or starches is advantageously used.

Administration can be carried out by any method known to a person skilled in the art, preferably by the oral route or by injection, typically by the intraperitoneal, intracerebral, intrathecal, intravenous, intra-arterial or intramuscular route. Administration by the oral route is preferred. In the case of long-term treatment, the preferred route of administration will be sublingual, oral or transcutaneous.

For injection, the compounds are generally packaged in the form of liquid suspensions, which can be injected by means of syringes or by infusion, for example. It is to be understood that the flow rate and/or the dose injected, or in general the dose to be administered, can be adapted by a person skilled in the art depending on the patient, the pathology, the method of administration, etc. It is understood that repeated administrations can be performed, optionally in combination with other active ingredients or any pharmaceutically acceptable vehicle (buffers, saline, isotonic solutions, in the presence of stabilizers, etc.).

The invention is usable in mammals, in particular in humans.

The present invention further relates to a method for preparing a composition described above, characterized in that the active ingredient or active ingredients are mixed, by methods known per se, with acceptable, in particular pharmaceutically acceptable excipients.

The invention relates in particular to the use of a compound of formula (I) above, including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid in the preparation of a medicament intended for the treatment or prevention of pathologies or injuries associated with the degeneration or death of cells, particularly of cardiac cells and/or of neurons, whether the latter are natural or accidental.

The invention relates even more particularly to the use of a compound of formula (I) above, including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid in the preparation of a medicament intended for the treatment or prevention of necrosis and/or of pathological apoptosis and/or of necroptosis (antinecrotic and/or antiapoptotic and/or antinecroptotic medicaments) or for the treatment or prevention of disorders such as:

diseases of the bones, joints, connective tissue and cartilage, such as osteoporosis, osteomyelitis, arthritis including for example osteoarthritis, rheumatoid arthritis and psoriatic arthritis, avascular necrosis, fibrodysplasia ossificans progressiva, rickets, Cushing's syndrome;

muscular diseases such as muscular dystrophy, for example Duchenne muscular dystrophy, myotonic dystrophies, myopathies and myasthenias;

skin diseases, such as dermatitis, eczema, psoriasis, ageing, or impaired healing;

cardiovascular diseases such as cardiac and/or vascular ischaemia, myocardial infarction, ischaemic cardiopathy, chronic or acute heart failure, cardiac dysrhythmia, atrial fibrillation, ventricular fibrillation, paroxysmal tachycardia, heart failure, hypertrophic cardiomyopathy, anoxia, hypoxia, side effects due to therapy with anticancer agents, cardiac lesions associated with reperfusion following accidental or induced (surgical intervention) ischaemia;

circulatory diseases such as atherosclerosis, arterial scleroses, and peripheral vascular diseases, cerebrovascular accidents, aneurysms;

haematological and vascular diseases such as: anaemia, vascular amyloidosis, haemorrhages, drepanocytosis, red cell fragmentation syndrome, neutropenia, leukopenia, bone marrow aplasia, pancytopenia, thrombocytopenia, haemophilia;

lung diseases including pneumonia, asthma; chronic obstructive pulmonary diseases for example chronic bronchitis and emphysema;

diseases of the gastrointestinal tract, such as ulcers;

diseases of the liver for example hepatitis particularly hepatitis of viral origin or having other infectious agents as the causative agent, alcoholic hepatitis, autoimmune hepatitis, fulminant hepatitis, certain hereditary metabolic disorders, Wilson's disease, cirrhoses, alcoholic liver disease (ALD), liver diseases due to toxins or medication; steatoses for example:

non-alcoholic steatohepatitis (NASH), or that accompanying exogenous intoxication with alcohol or medicaments, viral or toxic hepatitis, complications of surgical procedures, metabolic diseases (such as diabetes, glucose intolerance syndrome, obesity, hyperlipidaemias, dysfunctions of the hypothalamic-hypophyseal axis, abetalipoproteinaemia, galactosaemias, glycogen diseases, Wilson's disease, Weber-Christian disease, Ref sum syndrome, carnitine deficiency), hepatic complications of inflammatory diseases of the alimentary canal, autoimmune hepatitis.

Through action on steatosis or action on hepatic apoptosis, whatever its cause, the compounds could have a preventive effect on the development of hepatic fibrosis and prevention of occurrence of cirrhoses and diseases of the pancreas, for example acute or chronic pancreatitis;

metabolic diseases such as diabetes mellitus and diabetes insipidus, thyroiditis;

kidney diseases, such as for example acute renal disorders or glomerulonephritis;

viral and bacterial infections such as septicaemia;

severe intoxications with chemicals, toxins or drugs;

degenerative disorders associated with acquired immunodeficiency syndrome (AIDS);

disorders associated with ageing, such as accelerated ageing syndrome;

inflammatory diseases, such as Crohn's disease, rheumatoid arthritis;

autoimmune diseases such as lupus erythematosus;

dental disorders such as those resulting in tissue degradation, for example periodontitis;

ophthalmic diseases or disorders including diabetic retinopathies, glaucoma, macular degeneration, retinal degeneration, retinitis pigmentosa, holes or tears in the retina, detachment of the retina, retinal ischaemia, acute retinopathies associated with an injury, inflammatory degeneration, postoperative complications, medicament-induced retinopathies, cataract;

disorders of the auditory tract, such as otosclerosis and antibiotic-induced deafness;

diseases associated with the mitochondria (mitochondrial pathologies), such as Friedreich's ataxia, congenital muscular dystrophy with mitochondrial structural abnormalities, certain myopathies (MELAS syndrome, MERFF syndrome, Pearson syndrome), MIDD syndrome (maternally inherited diabetes and deafness), Wolfram syndrome, dystonia, and particularly neurodegenerative diseases for example Huntington's disease, chronic neurodegenerative diseases, advantageously chronic demyelinating diseases and neurodegenerative, hereditary or sporadic, in particular multiple sclerosis and leukodystrophies, neuronal lesions connected with ageing, hereditary or lesion-induced peripheral neuropathies, Charcot-Marie-Tooth disease, diabetic neuropathies or those induced by anticancer treatments, epilepsy, injuries of the brain, of the peripheral nerves or of the spinal cord, ischaemias of the brain or of the spinal cord, degeneration that is hereditary, lesional or connected with ageing of the sensory neurons of vision or degeneration of the optic nerve, degeneration that is hereditary, traumatic or connected with ageing of the sensory neurons of hearing, lobar atrophies and vascular dementias, diseases and injuries associated with degeneration of motoneurons and more particularly spinal muscular atrophy, particularly infantile, amyotrophic lateral sclerosis, multiple sclerosis and injuries of the spinal cord or of peripheral motor nerves.

The invention relates quite particularly to the use of a compound of formula (I), including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid in the preparation of a medicament intended for the treatment of spinal muscular atrophy, particularly infantile, and of amyotrophic lateral scleroses.

The application of these medicaments usually comprises the administration to patients, particularly to mammals, quite particularly to human beings, of a therapeutically effective quantity of a compound of formula I, including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid, in particular for increasing the survival of cells, particularly of cardiac cells and/or of neurons or to promote axonal growth.

The invention further relates to a method of treatment of the aforementioned, in particular neurodegenerative, diseases and in particular a method of treatment of pathologies or injuries associated with degeneration or death of neurons, in mammals (generally patients) affected by said pathologies or injuries, comprising the administration, to these mammals, of a therapeutically effective quantity of a compound of formula I, including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid in particular for increasing the survival of neurons or for promoting axonal growth.

The invention further relates to a method of treatment of one of the disorders described above and in particular of pathologies or injuries associated with degeneration or death of motoneurons, in mammals (generally patients) affected by said pathologies or injuries, comprising the administration, to these mammals, of a therapeutically effective quantity of a compound of formula I, including 3,4-nor-2,5-secocholestan-5-one oxime, methyl 5-hydroxyimino-4-nor-3,5-secostigmastan-3-oate, methyl 5-hydroxyimino-4-nor-3,5-secocholestan-3-oate, 4,5-secocholestan-3-yn-5-one oxime, 24-methyl-A-nor-1,5-secocholest-22-en-5-one oxime, 4-methylidyne-4,5-secocholestan-5-one oxime, 4-methyl-4,5-secocholestan-3-yn-5-one oxime, methyl 5-hydroxyimino-4,5-secocholestan-4-oate, 3-acetyloxy-4-nor-3,5-secocholestan-5-one oxime and/or 24-N,N-diethylcarbamoyl-3,5-seco-4-norcholane-5-hydroxyimino-3-oic acid in particular for increasing the survival of neurons. More specifically, pathologies associated with the degeneration or death of motoneurons are amyotrophic lateral sclerosis or infantile spinal muscular atrophies.

According to another variant, the invention also relates to compounds having a labelling group that can be detected and/or visualized directly or indirectly by techniques of detection and/or of visualization known to a person skilled in the art, such as fluorescence microscopy or the technique that takes advantage of the very strong affinity of the avidins (streptavidin or neutravidin) for biotin (Ka~$10^7$M).

In the general sense of the term, "label" means an entity such as a radioactive isotope or a non-isotopic entity such as a fluorophore, a stain, a hapten, biotin, etc.

The term fluorophore generally refers to the characteristic of a substance of being fluorescent, i.e. of absorbing light energy (excitation light) when it is excited by an energy source and of quickly returning it in the form of fluorescent light (emission light). This characteristic of being a fluorophore makes it possible to envisage the use of said substance as a fluorescent label in biological systems (membranes, cells, neurons, mitochondria, etc.) for example for performing imaging of the cells under investigation.

Biotin is a coenzyme, also called vitamin H, synthesized by plants, bacteria and certain fungi. Biotin is detected by means of avidins (streptavidin or neutravidin), which possess very strong affinity for biotin (Ka~$10^7$M). The structure of biotin is as follows:

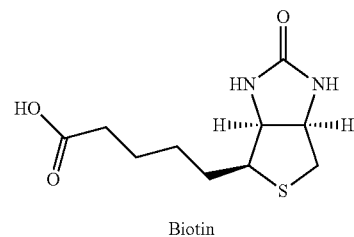 [SMILES: O=C(O)CCCC[C@@H]1SC[C@@H]2NC(=O)N[C@@H]21]

Biotin

It is known from the prior art that incorporation of a biotin group in a biologically active substance makes it possible to isolate and/or identify the protein targets or other non-protein compounds that can interact with said active substance, using an approach that takes advantage of the very strong affinity of the avidins for biotin. The protein targets or other non-protein compounds thus isolated are for example characterized by mass spectrometry. Among the applications known to a person skilled in the art, there may be mentioned for example: diagnostic tests using biotinylated compounds; ELISA (Enzyme-Linked Immunosorbent Assay) employing biotinylated antibiotics; affinity chromatography based on the use of a column of immobilized avidin on which biotinylated compounds are loaded; techniques of proteomic analysis (2D electrophoresis and mass spectrometry), etc.

The labelling group according to the present invention can be selected from biotin or a fluorophore group such as 7-nitrobenz-2-oxa-1,3-diazol-4-yl (formula D); BODIPY® fluorophore; anthracene and fluorescein. Preferably, the labelling group according to the present invention is selected from biotin and the fluorophore group 7-nitrobenz-2-oxa-1,3-diazol-4-yl (formula D).

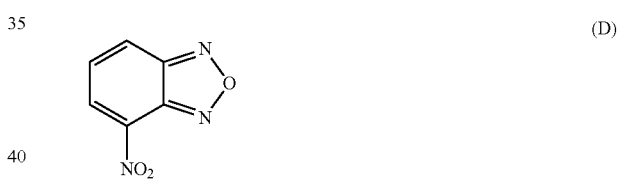

(D)

The compounds according to the present invention, labelled with biotin or with a fluorophore group, are very useful probes for:
visualizing and/or detecting cells that are in contact with the labelled compounds,
investigating their distribution in a living organism, human or animal, and their localization in the cellular compartments (membranes, cells, neurons, mitochondrion, nucleus, endoplasmic reticulum, Golgi apparatus, lysosomes, endosomes and other organelles, etc),
applying a method of detection of proteins or other non-protein compounds that can interact with said labelled compounds,
identifying their molecular target(s),
investigating molecule-protein interactions from a molecular standpoint,
detecting monoclonal antibodies specific to 3,5-seco-4-nor-cholestane oxime or its derivatives,
developing and carrying out binding assays making possible, among other things, the optimization of ligands with higher affinity for the target in question,
developing assaying methods,
developing new tools for screening ligands.

The incorporation of said labelling group did not cause loss of the biological activity of the labelled compounds according to the present invention and made it possible to use these labelled compounds as probes and in particular as tracers or labelling agents.

Consequently, another aim of the invention is to supply compounds of formula (I) having a labelling group selected from the group NBD and biotin.

The invention further relates to the use, as probes and in particular as tracers or labelling agents, of the compounds of formula I, for which:

$R_2$ can represent a group corresponding to the following formula (A):

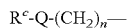  (A)

in which
  n can represent an integer that can take any one of the values from 1 to 8;
  Q can represent an oxygen atom or an —NR$^a$ group in which R$^a$ is as defined previously, and
  R$^c$ can represent a group corresponding to formula (C) or (D)

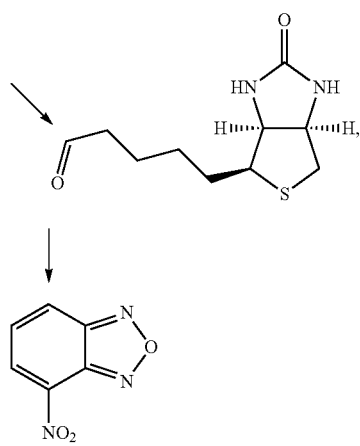

The compounds that are particularly preferred as tracers or labelling agents according to the invention are represented by the following formulae (II), (III):

The compounds of formula (I) according to the invention can be obtained by various methods of synthesis in particular employing the reaction of oximation of ketones, which is well known to a person skilled in the art. The scheme shown below illustrates the procedure used for preparing the compounds of formula (I)

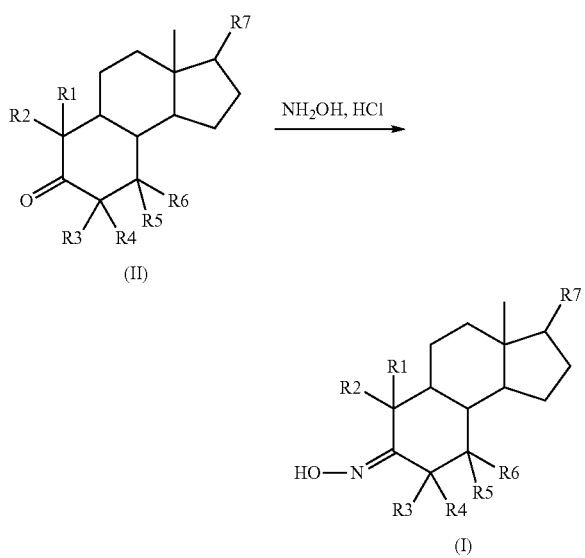

By way of example, a method that is particularly suitable for obtaining the compounds of formula (I) consists of reacting:
  (i) a compound of formula (II) in which the $R_1$ to $R_7$ groups are as defined previously, with
  (ii) a hydroxylamine halide such as hydroxylamine hydrochloride.

This method can advantageously be carried out in a suitable solvent such as pyridine.

The compounds of formula (I) can be isolated from the reaction medium by various methods that are well known to a person skilled in the art. Optionally, the compounds of formula (I) can be converted to one of their pharmaceutically

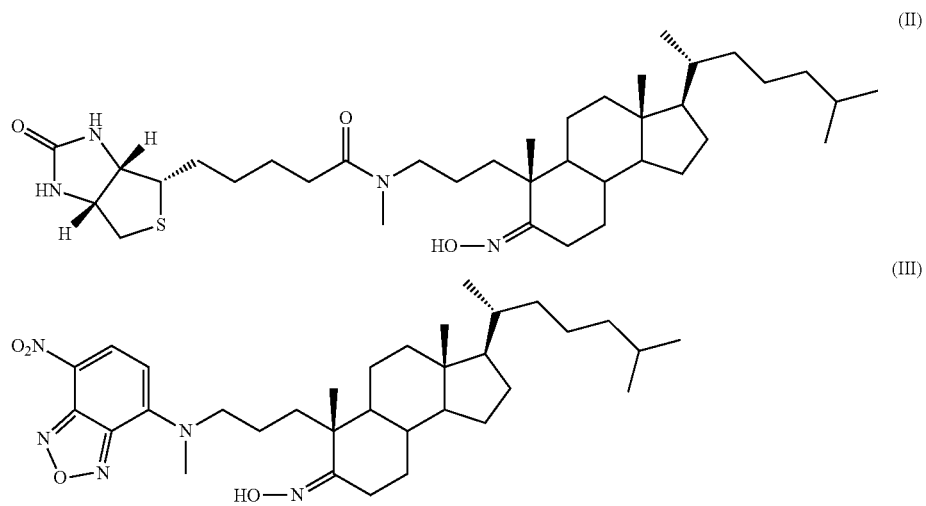

acceptable salts. The compounds of formula (II) used as starting products for obtaining the compounds of formula (I) are available commercially or are prepared by methods known to a person skilled in the art.

The following examples illustrate the present invention but without limiting it. The structures of the compounds described in the examples and in the preparations were determined by the usual techniques (nuclear magnetic resonance, mass spectroscopy, etc).

ABBREVIATIONS:

THF: tetrahydrofuran
AcOH: acetic acid
EtOAc: ethyl acetate
TBAF: tetrabutylammonium fluoride
DAST: (diethylamino)sulphur trifluoride
s: singlet
d: doublet
t: triplet
sept.: septuplet

EXAMPLE 1

Preparation of Compounds of Formula (II)

EXAMPLE 1a

Synthesis of
3,3-difluoro-3-methyl-4,5-secocholestan-5-one

Step i: Preparation of 3,3-difluoro-5,5-(ethylenedioxy)-4,5-secocholestane 290 mg (0.65 mmol) of 5,5-(ethylenedioxy)-4,5-secocholestan-3-one (WO2007/101925) is solubilized in 30 mL of dichloromethane, then 4 mL of DAST is added. The mixture is stirred under reflux for 2 days, cooled to 0° C. and hydrolysed by the dropwise addition of water. The mixture is then extracted with dichloromethane, the organic phases are combined, dried over anhydrous $MgSO_4$, filtered and concentrated under vacuum. The residue obtained is purified by silica-gel flash chromatography (petroleum ether/ethyl acetate 98/2 then 96/4). 64 mg (yield 55%) of the expected product is obtained in the form of brown oil.

$^1$H-NMR (CDCl$_3$) δ (ppm) 4.01-3.85 (m, 4H); 1.00 (s, 3H); 0.90 (d, 3H); 0.87 (dd, 6H); 0.67 (s, 3H)
MS (ESI+): m/z=469 [M+H]$^+$ Step ii: Preparation of
3,3-difluoro-4,5-secocholestan-5-one 169 mg (0.36 mmol) of 3,3-difluoro-5,5-(ethylenedioxy)-4,5-secocholestane is added to 15 mL of a 4N HCl solution in dioxane at 0° C. The mixture is then stirred for 2 h at 0° C. and then concentrated under vacuum. The residue obtained is purified by silica-gel flash chromatography (petroleum ether/ethyl acetate 98/2). 105 mg (yield 69%) of the expected product is obtained in the form of yellow oil.

$^1$H-NMR (CDCl$_3$) δ (ppm) 3.31 (dd, 1H); 1.09 (s, 3H); 0.90 (d, 3H); 0.86 (dd, 6H); 0.69 (s, 3H)
$^{19}$F-NMR (CDCl$_3$): δ (ppm, not calibrated)-86.35 (q)
MS (ESI+): m/z=440 [M+H]$^+$ EXAMPLE 1b Synthesis of
4-nor-3,5-secocholestan-3,25-diol-5-one Step i: Preparation of
3-acetyloxy-4-nor-3,5-secocholestan-25-ol-5-one A buffer solution pH=7 is prepared by mixing 10 mL of a 0.1M solution of $KH_2PO_4$ and 10 mL of a 0.1M NaOH solution.

200 mg (0.46 mmol) of 3-acetyloxy-4-nor-3,5-secocholestan-5-one* is put in 2 mL of $CCl_4$ and 2 mL of acetonitrile. 2.3 mL of previously prepared buffer solution is added, as well as 10.3 mg (0.046 mmol) of $RuCl_3.H_2O$ and 342 mg (1.6 mmol) of $NaIO_4$. The reaction medium is stirred for 5 days at 45° C., then extracted 3 times with dichloromethane. The organic phases are combined, washed with a saturated solution of NaCl in water, dried over anhydrous $MgSO_4$, filtered and concentrated under vacuum. The residue obtained is purified by silica-gel flash chromatography (petroleum ether/ethyl acetate 95/5). 51 mg (yield 24%) of the expected product is obtained in the form of colourless oil.

*3-Acetyloxy-4-nor-3,5-secocholestan-5-one is described in the article by Rodewald, W. J. et al. Bull. Acad. Pol. Sci., Série des Sciences Chimiques (1963), 11(8), 437-441

$^1$H-NMR (CDCl$_3$) δ (ppm) 4.03 (t, 2H); 2.05 (s, 3H); 1.21 (s, 6H); 1.08 (s, 3H); 0.92 (d, 3H); 0.72 (s, 3H)
MS (ESI+): m/z=371 [M–$H_2O$—AcOH+H]$^+$, 389 [M-AcOH+H]$^+$ Step ii: Preparation of
4-nor-3,5-secocholestan-3,25-diol-5-one A mixture of 50 mg (0.4 mmol) of 3-acetyloxy-4-nor-3,5-secocholestan-25-ol-5-one and 2.3 mL of a 5% KOH solution in methanol is stirred for 2.5 h at ambient temperature. The reaction medium is then immersed in water, stirred for 15 minutes at ambient temperature, then extracted 3 times with ethyl acetate. The organic phases are combined, washed with a saturated solution of NaCl in water, dried over anhydrous $MgSO_4$, filtered and concentrated under vacuum. The residue obtained is purified by silica-gel flash chromatography (petroleum ether/ethyl acetate 9/1 then 8/2). 21 mg (yield 46%) of the expected product is obtained in the form of yellow oil.

$^1$H-NMR (CDCl$_3$) δ (ppm) 4.12-3.86 (m, 1H); 3.73-3.53 (m, 1H); 1.21 (s, 6H); 1.08 (s, 3H); 0.92 (d, 3H); 0.66 (s, 3H)
MS (ESI+): m/z=389 [M–$H_2O$+H]$^+$, 447 [M+H]$^+$ EXAMPLE 1c Synthesis of 4-nor-3,5-seco-3-(trifluoromethyl) cholestan-3-ol-5-one Step i: Preparation of 4-nor-5,5-(ethylenedioxy)-3,5-seco-3-(trifluoromethyl)cholestan-3-ol 200 mg (0.46 mmol) of 5,5-(ethylenedioxy)-4-nor-3,5-secocholestan-3-al (WO2007/101925) and 277 µL (0.555 mmol) of (trifluoromethyl)trimethylsilane 2M in THF are placed in 3 mL of anhydrous THF under argon. The mixture is cooled to 0° C. and 10 µL of 1M TBAF in THF is added. The mixture is stirred for 24 h at ambient temperature and 0.3 mL of (trifluoromethyl)trimethylsilane 2M in THF is added. After a further 24 h at ambient temperature, 0.3 mL of (trifluoromethyl)trimethylsilane 2M in THF and 50 μL of 1M TBAF in THF are added. The mixture is stirred for 72 h at ambient temperature, then a 1N HCl solution is added. The mixture is then stirred for 15 minutes at ambient temperature, then extracted 3 times with ethyl acetate. The organic phases are combined, washed with water, with a saturated solution of NaCl in water, dried over anhydrous $MgSO_4$, filtered and then concentrated under vacuum. The residue obtained is purified by silica-gel flash chromatography (petroleum ether 100% then petroleum ether/ethyl acetate 95/5). 63 mg (yield 27%) of the expected product is obtained.

$^1$H-NMR (CDCl$_3$) δ (ppm) 4.02-3.84 (m, 4H); 3.83-3.67 (m, 1H); 1.00 (s, 3H); 0.91 (d, 3H); 0.86 (dd, 6H); 0.67 (s, 3H)

$^{19}$F-NMR (CDCl$_3$): δ (ppm)-80.30 (d)

MS (ESI+): m/z=443 [M-OCH$_2$CH$_2$O+H]$^+$

Step ii: Preparation of 4-nor-3,5-seco-3-(trifluoromethyl)norcholestan-3-ol-5-one 63 mg (0.125 mmol) of 4-nor-5,5-(ethylenedioxy)-3,5-seco-3-(trifluoromethyl)cholestan-3-ol is placed in a THF/H$_2$O/AcOH mixture (2 mL/2 mL/2.5 mL). The reaction medium is stirred for 2 days at ambient temperature, immersed in an H$_2$O/EtOAc mixture and extracted 3 times with ethyl acetate. The organic phases are combined, washed with a 10% solution of NaHCO$_3$, then with a saturated solution of NaCl in water, dried over anhydrous MgSO$_4$, filtered and concentrated under vacuum. The residue obtained is purified by silica-gel flash chromatography (petroleum ether/ethyl acetate 95/5). 21 mg (yield 37%) of the expected product is obtained in the form of a colourless oil, which is used as it is in the next step.

MS (ESI+): m/z=459 [M+H]$^+$, 481 [M+Na]$^+$

EXAMPLE 1d

Synthesis of 3-[(N-(+)-biotinoyl-N-methyl)amino]-4-nor-3,5-secocholestan-5-one

Step i: Preparation of 3-[N-(+)-biotinoyl-N-methyl)amino]-5,5-(ethylenedioxy)-4-nor-3,5-secocholestane 500 mg (1.1 mmol) of 5,5-(ethylenedioxy)-3-(N-methylamino)-4-nor-3,5-secocholestane (WO2007/101925), 232 mg (1.21 mmol) of 1-(3-dimethylaminopropyl)-3-ethylcarbodiimide hydrochloride, 309 mg (2.53 mmol) of N,N-dimethylaminopyridine and 327 mg (1.34 mmol) of D(+)-biotin in 80 mL of dichloromethane are introduced into a flask. The reaction medium is stirred for 48 h at ambient temperature and then it is washed with a 1M HCl solution, a saturated solution of sodium chloride, dried over anhydrous magnesium sulphate and concentrated under vacuum. After purification by silica-gel flash chromatography (dichloromethane/methanol 98/2 then 95/5), 432 mg of the amide is obtained with an HPLC purity of 70% and is used as it is in the next step.

MS (ESI+): m/z=674 [M+H]$^+$

Step ii: Preparation of 3-[(N-(+)-biotinoyl-N-methyl)amino]-4-nor-3,5-secocholestan-5-one 280 mg (0.41 mmol) of 3-[N-(+)-biotinoyl-N-methyl) amino]-5,5-(ethylenedioxy)-4-nor-3,5-secocholestane is added to 5 mL of a 4N HCl solution in dioxane at 0° C. The mixture is then stirred overnight at ambient temperature and then concentrated under vacuum. The residue obtained is purified by silica-gel flash chromatography (dichloromethane then dichloromethane/methanol 9/1). 146 mg (yield 55%) of the expected product is obtained.

MS (ESI+): m/z=630 [M+H]+

EXAMPLE 1e

Synthesis of 3-[methyl-(7-nitro-2,1,3-benzoxadiazol-4-yl)amino]-4-nor-3,5-secocholestan-5-one Step i: Preparation of 5,5-(ethylenedioxy)-3-[Methyl-(7-nitro-2,1,3-benzoxadiazol-4-yl)amino]-4-nor-3,5-secocholestane 200 mg (0.45 mmol) of 5,5-(ethylenedioxy)-3-(N-methylamino)-4-nor-3,5-secocholestane, 98 mg (0.49 mmol) of 4-chloro-7-nitrobenzofurazane and 125 μL of triethylamine in 15 mL of chloroform are introduced into a flask. The solution is stirred overnight at ambient temperature away from the light and then the reaction medium is washed with a 1M HCl solution, dried over anhydrous magnesium sulphate and concentrated under vacuum. The residue obtained is purified by silica-gel flash chromatography (dichloromethane). 150 mg (yield 43%) of the expected product is obtained.

$^1$H-NMR (CDCl$_3$) δ (ppm) 8.45 (d, 1H); 6.06 (d, 1H); 4.07-3.69 (m, 6H); 3.54-3.35 (m, 3H); 0.99 (s, 3H); 0.90 (d, 3H); 0.86 (dd, 6H); 0.66 (s, 3H)

Step ii: Preparation of 3-[methyl-(7-nitro-2,1,3-benzoxadiazol-4-yl)amino]-4-nor-3,5-secocholestan-5-one 110 mg (0.18 mmol) of 5,5-(ethylenedioxy)-3-[methyl-(7-nitro-2,1,3-benzoxadiazol-4-yl)amino]-4-nor-3,5-secocholestane is added to 4 mL of a 4N HCl solution in dioxane at 0° C. The mixture is then stirred overnight at ambient temperature and then concentrated under vacuum. The residue obtained is purified by silica-gel flash chromatography (dichloromethane). 65 mg (yield 63%) of the expected product is obtained.

$^1$H-NMR (CDCl$_3$) δ (ppm) 8.47 (d, 1H); 6.13 (d, 1H); 4.08-3.80 (m, 2H); 3.60-3.38 (m, 3H); 1.11 (s, 3H); 0.91 (d, 3H); 0.86 (dd, 6H); 0.73 (s, 3H)

EXAMPLE 1f

Synthesis of 25-fluoro-4-nor-3,5-secocholestan-3-ol-5-one

Step i: Preparation of 25-fluorocholest-4-en-3-one 100 mg (0.247 mmol) of 25-fluorocholest-5-en-3β-ol* and 15 mL of acetone are introduced into a flask at 0° C., and then 160 μL of Jones reagent is added. The mixture is stirred for 9 minutes at 0° C. and then the reaction is stopped by adding ethanol. After concentration under vacuum at a temperature below 30° C., the residue is taken up in 10 mL of ethanol, and 100 μL of a 1N solution of hydrochloric acid is added. The mixture is stirred for 15 minutes at 50-60° C. and then concentrated under vacuum. The residue obtained is taken up in water and extracted with ethyl acetate; the organic phase is separated, washed with water, dried over anhydrous magnesium sulphate and concentrated under vacuum. After purification by silica-gel flash chromatography (petroleum ether then petroleum ether/ethyl acetate 95/5), 69 mg of the enone is obtained with a yield of 69%.

*25-Fluorocholest-5-en-3β-ol is available from Steraloids Inc. (Wilton, N.H.)

LC/UV/MS (254 nm): T$_R$=5.41 min, m/z=403 [M+H]$^+$

Step ii: Preparation of 25-fluoro-4-nor-5-oxo-3,5-secocholestan-3-oic acid 77 mg of 25-fluoro-4-cholesten-3-one is solubilized in 7 mL of hot tert-butanol, then 79 mg (0.57 mmol) of $K_2CO_3$ is added. A solution of 12 mg (0.076 mmol) of $KMnO_4$ and 191 mg (0.89 mmol) of $NaIO_4$ in 7 mL of water is prepared at 60° C., then poured dropwise into the reaction medium without exceeding 40° C. The reaction medium is then stirred at ambient temperature for 1 h. After cooling, the excess oxidizing agent is destroyed by adding solid $NaHSO_3$. The mixture is acidified to pH=1 by adding a 1N HCl solution, then extracted 3 times with diethyl ether. The organic phases are combined, washed with a solution of $Na_2S_2O_3$ in water, and with a saturated solution of NaCl, dried over anhydrous magnesium sulphate and concentrated under vacuum. 92 mg of acid is obtained and is used as it is in the next step.

$^1$H-NMR ($CDCl_3$) δ (ppm) 1.34 (d, 6H); 1.12 (s, 3H); 0.92 (d, 3H); 0.73 (s, 3H)

MS (ESI+): m/z=423 $[M+H]^+$

Step iii: Preparation of methyl 25-fluoro-4-nor-5-oxo-3,5-secocholestan-3-oate 92 mg (0.218 mmol) of 25-fluoro-4-nor-5-oxo-3,5-secocholestan-3-oic acid is solubilized in 1 mL of methanol and 3 mL of dichloromethane. At 0° C., 48 μL (0.653 mmol) of thionyl chloride is added and the mixture is stirred for 2 h at 0° C. The reaction medium is then concentrated under vacuum, co-evaporated with toluene then with dichloromethane. 78 mg of ester (yield 82%) is obtained and is used as it is in the next step.

$^1$H-NMR ($CDCl_3$) δ (ppm) 3.66 (s, 3H); 2.65-2.50 (m, 1H); 2.40-2.26 (m, 1H); 1.33 (d, 6H); 1.11 (s, 3H); 0.92 (d, 3H); 0.67 (s, 3H)

MS (ESI+): m/z=437 $[M+H]^+$

Step iv: Preparation of methyl 5,5-(ethylenedioxy)-25-fluoro-4-nor-3,5-secocholestan-3-oate 123 mg (0.282 mmol) of methyl 25-fluoro-4-nor-5-oxo-3,5-secocholestan-3-oate is dissolved in 2 mL of trimethylorthoformate and 2 mL of ethylene glycol. 5.4 mg (0.028 mmol) of anhydrous p-toluenesulphonic acid is added, then the mixture is stirred overnight at ambient temperature. The reaction medium is immersed in ethyl acetate, washed with a 10% solution of $NaHCO_3$, then with a saturated solution of NaCl, dried over anhydrous $MgSO_4$, filtered and concentrated under vacuum. The residue obtained is purified by silica-gel flash chromatography (petroleum ether/ethyl acetate 95/5). 74 mg (yield 54%) of the expected product is obtained in the form of yellow oil.

$^1$H-NMR ($CDCl_3$) δ (ppm) 3.98-3.87 (m, 4H); 3.64 (s, 3H); 2.65-2.50 (m, 1H); 2.40-2.26 (m, 1H); 1.34 (d, 6H); 0.99 (s, 3H); 0.91 (d, 3H); 0.66 (s, 3H)

Step v: Preparation of 5,5-(ethylenedioxy)-25-fluoro-4-nor-3,5-secocholestan-3-ol 385 μL (0.385 mmol) of a 1N solution of $LiAlH_4$ in THF and 1 mL of anhydrous THF are introduced into a flask, under argon. A solution of 74 mg (0.154 mmol) of methyl 5,5-(ethylenedioxy)-25-fluoro-4-nor-3,5-secocholestan-3-oate in 1 mL of anhydrous THF is added dropwise at 0° C. to the solution of $LiAlH_4$ in THF. The reaction medium is stirred for 1 h at 0° C. and then hydrolysed slowly at 0° C. by adding a saturated solution of $Na_2SO_4$. The mixture is then taken up in ethyl acetate, washed with a 10% solution of $NaHCO_3$, then with a saturated solution of NaCl, dried over anhydrous $MgSO_4$, filtered and concentrated under vacuum. 63 mg (yield 90%) of the expected product is obtained in the form of oil.

$^1$H-NMR ($CDCl_3$) δ (ppm) 4.00-3.86 (m, 4H); 3.55 (t, 2H); 1.33 (d, 6H); 0.98 (s, 3H); 0.91 (d, 3H); 0.66 (s, 3H)

Step vi: Preparation of 25-fluoro-4-nor-3,5-secocholestan-3-ol-5-one 63 mg (0.139 mmol) of 5,5-(ethylenedioxy)-25-fluoro-4-nor-3,5-secocholestan-3-ol is placed in a $THF/H_2O/AcOH$ mixture (1 mL/1 mL/2 mL). The reaction medium is stirred overnight at ambient temperature, immersed in ethyl acetate, washed with a saturated solution of $NaHCO_3$, dried over anhydrous $MgSO_4$, filtered and concentrated under vacuum. The residue obtained is purified by silica-gel flash chromatography (petroleum ether/ethyl acetate 98/2 then 95/5). 17 mg (yield 29%) of the expected product is obtained in the form of a solid.

$^1$H-NMR ($CDCl_3$) δ (ppm) 4.15-3.49 (m, 2H); 1.33 (d, 6H); 0.92 (d, 3H); 0.65 (s, 3H)

MS (ESI+): m/z=391 $[M-H_2O+H]^+$, 409 $[M+H]^+$

EXAMPLE 1g

Synthesis of 4-nor-3,5-secocholestan-5-one

Step i: Preparation of 5,5-(ethylenedioxy)-4-nor-3,5-seco-3-(tosyloxy)cholestane 1 g (2.3 mmol) of 5,5-(ethylenedioxy)-4-nor-3,5-secocholestan-3-ol (WO2007/101925) is dissolved in 3.5 mL of chloroform at 0° C., then 0.39 mL of pyridine and 675 mg (3.54 mmol) of tosyl chloride are added. The reaction medium is stirred for 2 h at 0° C. and overnight at ambient temperature. 7 mL of diethyl ether and 2 mL of water are added to the mixture. The organic phase is decanted, washed with a 2N HCl solution, then with a 5% solution of $NaHCO_3$, dried over anhydrous $MgSO_4$, filtered and concentrated under vacuum. 1 g of the expected product is obtained with an HPLC purity of 83% and is used as it is in the next step.

$^1$H-NMR ($CDCl_3$) δ (ppm) 7.78 (d, 2H); 7.34 (d, 2H); 4.00-3.77 (m, 6H); 2.44 (s, 3H); 0.91 (s, 3H); 0.90 (d, 3H); 0.86 (dd, 6H); 0.64 (s, 3H)

Step ii: Preparation of 5,5-(ethylenedioxy)-4-nor-3,5-secocholestane 1 mL (1 mmol) of a 1N solution of $LiAlH_4$ in THF and 3 mL of anhydrous diethyl ether are introduced into a flask, under nitrogen. A solution of 500 mg (0.72 mmol) of 5,5-(ethylenedioxy)-4-nor-3,5-seco-3-(tosyloxy)cholestane in 2 mL of anhydrous diethyl ether is added dropwise at 0° C. to the solution of $LiAlH_4$. The reaction medium is stirred for 2 h under reflux and then hydrolysed slowly at 0° C. by adding a saturated solution of $Na_2SO_4$. The mixture is then taken up in water and extracted 3 times with diethyl ether. The organic phases are combined, washed with a saturated solution of NaCl, dried over anhydrous $MgSO_4$, filtered and concentrated under vacuum. The residue obtained is purified by silica-gel flash chromatography (petroleum ether 100% then petroleum ether/ethyl acetate 98/2, then 95/5). 258 mg of the expected product is obtained with an HPLC purity of 85% and is used as it is in the next step.

¹H-NMR (CDCl₃) δ (ppm) 3.98-3.85 (m, 4H); 1.96 (d, 1H); 1.88-1.74 (m, 1H); 0.95 (s, 3H); 0.89 (d, 3H); 0.86 (dd, 6H); 0.81 (t, 3H); 0.66 (s, 3H)
MS (ESI+): m/z=419 [M+H]⁺

Step iii: Preparation of
4-nor-3,5-secocholestan-5-one 250 mg (0.506 mmol) of 5,5-(ethylenedioxy)-4-nor-3,5-secocholestane is placed in a THF/H₂O/AcOH mixture (2 mL/2 mL/5 mL). The reaction medium is stirred overnight at ambient temperature, immersed in ethyl acetate, washed with a 10% solution of NaHCO₃, dried over anhydrous MgSO₄, filtered and concentrated under vacuum. The residue obtained is purified by silica-gel flash chromatography (petroleum ether/diethyl ether 99/1). 89 mg (yield 41%) of the expected product is obtained.
¹H-NMR (CDCl₃) δ (ppm) 2.51 (td, 1H); 2.25 (ddd, 1H); 1.05 (s, 3H); 0.91 (d, 3H); 0.86 (dd, 6H); 0.72 (s, 3H)

EXAMPLE 1h

Synthesis of 4-nor-3,5-secocholest-6-en-5-one and of 7-hydroxyamino-4-nor-3,5-secocholestan-5-one oxime Step i: Preparation of
6-bromo-4-nor-3,5-secocholestan-3-ol-5-one 5.2 g (17.3 mmol) of 4-nor-3,5-secocholestan-3-ol-5-one (WO2007/101925) is dissolved in 91 mL of dioxane and 10 mL of water. 5.45 g (30.6 mmol) of N-bromosuccinimide is added and the reaction medium is stirred for 10 h at 50° C., then overnight at 30° C. The solution is concentrated under vacuum, the residue is taken up in water and extracted 3 times with dichloromethane. The organic phases are combined, washed with a saturated solution of NaCl, dried over anhydrous MgSO₄, filtered and concentrated under vacuum. The residue obtained is purified by silica-gel flash chromatography (petroleum ether/ethyl acetate gradient 10/0 to 9/1). 4.88 g (yield 78%) of the expected product is obtained.
¹H-NMR (CDCl₃) δ (ppm) 4.49-4.37 (m, 1H); 4.15-3.91 (m, 1H); 3.79-3.68 (m, 1H); 0.95 (s, 3H); 0.90 (d, 3H); 0.86 (dd, 6H); 0.64 (s, 3H)
MS (ESI+): m/z=451/453 [M−H₂O+H]⁺

Step ii: Preparation of
4-nor-3,5-secocholest-6-en-3-ol-5-one 4.88 g (10.4 mmol) of 6-bromo-4-nor-3,5-secocholestan-3-ol-5-one is dissolved in 53 mL of anhydrous N,N-dimethylformamide, then 5.73 g of lithium bromide and 5.73 g of lithium carbonate are added. The reaction medium is stirred for 6.5 h at 100° C. and then overnight at 30° C. After cooling, the mixture is immersed in diethyl ether, and the precipitate is filtered. The filtrate is washed twice with a 0.1 HCl solution and then twice with water. The organic phase is separated, dried over anhydrous MgSO₄, filtered and concentrated under vacuum. The residue obtained is purified by silica-gel flash chromatography (dichloromethane/ethyl acetate gradient 10/0 to 8/2). 1.5 g (yield 37%) of the expected product is obtained.
¹H-NMR (CDCl₃) δ (ppm) 6.81 (dd, 1H); 5.92 (dd, 1H); 3.68-3.42 (m, 2H); 1.00 (s, 3H); 0.92 (d, 3H); 0.87 (dd, 6H); 0.76 (s, 3H)

EXAMPLE 1i

Synthesis of 3,4-dinor-2,5-secocholestan-2-ol-5-one

Step i: Preparation of methyl
3,4-dinor-5-methoxy-2,5-secocholest-5-en-2-oate 500 mg (1.28 mmol) of 3,4-dinor-5-oxo-2,5-secocholestan-2-oic acid* and 12 mg of APTS are placed in 7 mL of methanol. The reaction medium is then heated for 2 h under reflux, then 423 μL of trimethylorthoformate is added. Heating is continued for 2.5 h and 423 μL of trimethylorthoformate is added and the mixture is heated under reflux for a further 3 h. After cooling, powdered potassium carbonate is added to the mixture, then the latter is concentrated under vacuum. The residue is taken up in water and extracted twice with ethyl acetate. The organic phases are combined, washed with a saturated solution of NaCl, dried over anhydrous MgSO₄, filtered and concentrated under vacuum. The residue obtained is purified by silica-gel flash chromatography (petroleum ether 100% then petroleum ether/ethyl acetate 95/5). 331 mg (yield 62%) of the expected product is obtained.
*3,4-Dinor-5-oxo-2,5-secocholestan-2-oic acid is described in the following articles: Arencibia, M. T. et al. J. Chem. Soc., Perkin Trans. 1, (1991), 12, 3349-60 Conca, R. J. et al. J. Org. Chem., (1953), 18, 1104-111.
¹H-NMR (CDCl₃) δ (ppm) 3.58 (s, 3H); 3.45 (s, 3H); 2.74 (d, 1H); 2.31 (d, 1H); 1.06 (s, 3H); 0.90 (d, 3H); 0.85 (dd, 6H); 0.66 (s, 3H)
MS (ESI+): m/z=405 [M−CH₂+H]⁺

Step ii—Preparation of
3,4-dinor-5-methoxy-2,5-secocholest-5-en-2-ol 1.95 mL (1.95 mmol) of a 1N solution of LiAlH₄ in THF is introduced into a flask, under argon. A solution of 327 mg (0.781 mmol) of methyl 3,4-dinor-5-methoxy-2,5-secocholest-5-en-2-oate in 4 mL of anhydrous THF is added dropwise at 0° C. to the solution of LiAlH₄. The reaction medium is stirred for 30 minutes at 0° C. and then hydrolysed slowly at 0° C. by adding a saturated solution of Na₂SO₄. The mixture is then extracted 3 times with ethyl acetate, the organic phases are combined, washed with a saturated solution of NaCl, dried over anhydrous MgSO₄, filtered and concentrated under vacuum. 310 mg of the expected product is obtained and is used as it is in the next step.
MS (ESI+): m/z=359 [M−OCH₃]⁺

Step iii: Preparation of
3,4-dinor-2,5-secocholestan-2-ol-5-one 305 mg (0.78 mmol) of 3,4-dinor-5-methoxy-2,5-secocholest-5-en-2-ol is placed in a THF/H₂O/AcOH mixture (2 mL/2 mL/6 mL). The reaction medium is stirred overnight at ambient temperature, immersed in ethyl acetate and extracted 3 times with ethyl acetate. The organic phases are combined, washed with a 10% solution of NaHCO₃, then with a saturated solution of NaCl in water, dried over anhydrous MgSO₄, filtered and concentrated under vacuum. The residue obtained is purified by silica-gel flash chromatography (petroleum ether/ethyl acetate 95/5). 245 mg (yield 83%) of the expected product is obtained in the form of a colourless oil.
¹H-NMR (CDCl₃) δ (ppm) 4.01-3.78 (m, 2H); 1.02 (s, 3H); 0.90 (d, 3H); 0.86 (dd, 6H); 0.68 (s, 3H)
MS (ESI+): m/z=359 [M−H₂O+H]⁺

EXAMPLE 2

Synthesis of Compounds of Formula (I)

General Method A:

1 equivalent of ketone and 6 equivalents of hydroxylamine hydrochloride in pyridine (about 10 to 20 mL/mmol) is introduced into a flask. The solution is stirred overnight at ambient temperature, then the reaction medium is concentrated under vacuum. The residue obtained is taken up in water and extracted with dichloromethane or with ethyl acetate; the organic phase is separated, washed with water, dried over anhydrous $MgSO_4$ and concentrated under vacuum. If necessary, the product is purified by silica-gel flash chromatography.

Compound 1: 3,3-difluoro-4,5-secocholestan-5-one oxime

The oxime of 3,3-difluoro-4,5-secocholestan-5-one is obtained from 3,3-difluoro-4,5-secocholestan-5-one (product from Example 1a-step ii) with a yield of 87% according to method A.

$^1$H-NMR ($CDCl_3$) δ (ppm) 2.56 (td, 1H); 2.23 (dd, 1H); 1.09 (s, 3H); 0.90 (d, 3H); 0.85 (dd, 6H); 0.71 (s, 3H)

$^{19}$F-NMR ($CDCl_3$): δ (ppm, not calibrated)-86.14 (q)

MS (ESI+): m/z=405 [M−$H_2O$+H]$^+$, 447 [M+Na]$^+$

Compound 2: 4-nor-3,5-secocholestan-3,25-diol-5-one oxime

The oxime of 4-nor-3,5-secocholestan-3,25-diol-5-one is obtained from 4-nor-3,5-secocholestan-3,25-diol-5-one (product from Example 1b-step ii) with a yield of 63% according to method A.

$^1$H-NMR ($CDCl_3$) δ (ppm) 3.76-3.52 (m, 2H); 2.43-3.27 (dd, 1H); 1.21 (s, 6H); 1.07 (s, 3H); 0.92 (d, 3H); 0.70 (s, 3H)

MS (ESI+): m/z=422 [M+H]$^+$

Compound 3: 4-nor-3,5-seco-3-(trifluoromethyl)cholestan-3-ol-5-one oxime

The oxime of 4-nor-3,5-seco-3-(trifluoromethyl)cholestan-3-ol-5-one is obtained from 4-nor-3,5-seco-3-(trifluoromethyl)cholestan-3-ol-5-one (product from Example 1c-step ii) with a yield of 91% according to method A.

$^1$H-NMR ($CDCl_3$) δ (ppm) 4.05-3.80 (m, 1H); 3.36 (dd, 1H); 1.10 (s, 3H); 0.91 (d, 3H); 0.87 (dd, 6H); 0.70 (s, 3H)

$^{19}$F-NMR ($CDCl_3$): δ (ppm)-79.59 (d); −80.96 (d)

MS (ESI+): m/z=474 [M+H]$^+$

Compound 4: 3-[(N-(+)-biotinoyl-N-methyl)amino]-4-nor-3,5-secocholestan-5-one oxime The oxime of 3-[(N-(+)-biotinoyl-N-methyl)amino]-4-nor-3,5-secocholestan-5-one is obtained from 3-[(N-(+)-biotinoyl-N-methyl)amino]-4-nor-3,5-secocholestan-5-one (product from Example 1d-step ii) with a yield of 25% according to method A.

$^1$H-NMR ($CDCl_3$) δ (ppm) 4.60-4.47 (m, 1H); 4.40-4.28 (m, 1H); 3.49-3.25 (m, 2H); 3.23-3.10 (m, 1H); 2.90 (s, 3H); 2.73 (d, 1H); 2.51-2.21 (m, 2H); 1.06 (s, 3H); 0.91 (d, 3H); 0.86 (dd, 6H); 0.70 (s, 3H)

MS (ESI+): m/z=645 [M+H]$^+$

Compound 5: 3-[methyl-(7-nitro-2,1,3-benzoxadiazol-4-yl)amino]-4-nor-3,5-secocholestan-5-one oxime The oxime of 3-[methyl-(7-nitro-2,1,3-benzoxadiazol-4-yl)amino]-4-nor-3,5-secocholestan-5-one is obtained from 3-[methyl-(7-nitro-2,1,3-benzoxadiazol-4-yl)amino]-4-nor-3,5-secocholestan-5-one (product from Example 1e-step ii) with a yield of 87% according to method A.

$^1$H-NMR ($CDCl_3$) δ (ppm) 8.37 (d, 1H); 6.09 (d, 1H); 4.09-3.79 (m, 2H); 3.65-3.39 (m, 3H); 3.31 (dd, 1H); 1.09 (s, 3H); 0.90 (d, 3H); 0.85 (dd, 6H); 0.70 (s, 3H).

MS (ESI+): m/z=582 [M+H]$^+$

Compound 6: 25-fluoro-4-nor-3,5-secocholestan-3-ol-5-one oxime

The oxime of 25-fluoro-4-nor-3,5-secocholestan-3-ol-5-one is obtained from 25-fluoro-4-nor-3,5-secocholestan-3-ol-5-one (product from Example 1f-step yl) with a yield of 34% according to method A.

$^1$H-NMR ($CDCl_3$) δ (ppm) 3.75-3.53 (m, 2H); 3.36 (dd, 1H); 1.33 (d, 6H); 1.07 (s, 3H); 0.92 (d, 3H); 0.70 (s, 3H)

MS (ESI+): m/z=424 [M+H]$^+$

Compound 7: 4-nor-3,5-secocholestan-5-one oxime

The oxime of 4-nor-3,5-secocholestan-5-one is obtained from 4-nor-3,5-secocholestan-5-one (product from Example 1g-step iii) with a yield of 20% according to method A.

$^1$H-NMR ($CDCl_3$) δ (ppm) 3.40-3.26 (m, 1H); 2.00 (d, 1H); 1.04 (s, 3H); 0.91 (d, 3H); 0.86 (dd, 6H); 0.69 (s, 3H)

MS (ESI+): m/z=390 [M+H]$^+$

Compound 8: 4-nor-3,5-secocholest-6-en-3-ol-5-one oxime, and

Compound 9: 7-hydroxyamino-4-nor-3,5-secocholest-6-year-3-ol-5-one oxime 195 mg (0.502 mmol) of 4-nor-3,5-secocholest-6-en-3-ol-5-one (product from Example 1h-step ii) and 200 mg of hydroxylamine hydrochloride are added to 2 mL of pyridine. The solution is stirred overnight at ambient temperature, then 200 mg of hydroxylamine hydrochloride and 2 mL of pyridine are added. The reaction medium is stirred overnight again at ambient temperature, then it is concentrated under vacuum.

The residue is taken up in water and extracted 3 times with ethyl acetate. The organic phases are combined, washed with a saturated solution of NaCl, dried over anhydrous $MgSO_4$, filtered and concentrated under vacuum.

The residue obtained is purified by silica-gel flash chromatography (dichloromethane 100% then dichloromethane/ethyl acetate 8/2) in order to obtain 65 mg of 4-nor-3,5-secocholest-6-en-3-ol-5-one oxime (compound 8).

$^1$H-NMR ($CDCl_3$) δ (ppm) 6.79 (dd, 1H); 6.22 (d, 1H); 3.67-3.52 (m, 2H); 1.03 (s, 3H); 0.93 (d, 3H); 0.88 (dd, 6H); 0.75 (s, 3H)

MS (ESI+): m/z=404 [M+H]$^+$

Elution is carried out with a dichloromethane/methanol 95/5 eluent in order to obtain 71 mg of 7-hydroxyamino-4-nor-3,5-secocholest-6-year-3-ol-5-one oxime (compound 9).

$^1$H-NMR ($CDCl_3$) δ (ppm) 3.82 (dd, 1H); 3.74-3.50 (m, 2H); 3.28-3.19 (m, 1H); 1.10 (s, 3H); 0.87 (dd, 6H); 0.70 (s, 3H)

MS (ESI+): m/z=437 [M+H]$^+$

Compound 10: Preparation of 3,4-dinor-2,5-secocholestan-2-ol-5-one oxime

The oxime of 3,4-dinor-2,5-secocholestan-2-ol-5-one is obtained from 3,4-dinor-2,5-secocholestan-2-ol-5-one (product from Example 1i-step iii) with a yield of 81% according to method A.

$^1$H-NMR ($CDCl_3$) δ (ppm) 3.85-3.54 (m, 2H); 3.37 (dd, 1H); 1.09 (s, 3H); 0.86 (dd, 6H); 0.68 (s, 3H)

MS (ESI+): m/z=392 [M+H]$^+$

Compound 11: Preparation of 4-nor-3,5-secocholest-24-en-3-ol-5-one oxime

The oxime of 4-nor-3,5-secocholest-24-en-3-ol-5-one is obtained from 4-nor-3,5-secocholest-24-en-3-ol-5-one with a yield of 74% according to method A. Preparation of 4-nor-3,5-secocholest-24-en-3-ol-5-one is described in international application WO2008/056059.

$^1$H-NMR ($CDCl_3$) δ (ppm) 5.09 (t, 1H); 3.77-3.55 (m, 2H); 3.36 (dd, 1H); 1.68 (s, 3H); 1.60 (s, 3H); 1.08 (s, 3H); 0.92 (d, 3H); 0.70 (s, 3H)

MS (ESI+): m/z=404 [M+H]$^+$

Compound 12: Preparation of 24β-ethyl-4-nor-3,5-secocholest-22-en-3-ol-5-one oxime The oxime of 24β-ethyl-4-nor-3,5-secocholest-22-en-3-ol-5-one is obtained from 4-nor-3,5-secocholest-24-en-3-ol-5one with a yield of 88% according to method A. Preparation of 24β-ethyl-4-nor-3,5-secocholest-22-en-3-ol-5-one is described in patent WO2008/056059.

MS (ESI+): m/z=432 [M+H]$^+$

Pharmacological Investigation

The compounds were tested according to the following protocols:

Effects of the Compounds of Formula (I) on Survival of Motoneurons

To demonstrate the neuroprotective action of the compounds of formula (I), the applicant investigated their activity on a model in vitro of trophic deprivation of motoneurons in rats. It may be useful to refer to patent application WO 0142784 of the applicant regarding culture of the motoneurons of the spinal cord.

The spinal cord of E14 rat embryos is dissected and the ventral part is dissociated by trituration after trypsinization.

The motoneurons are separated from the other spinal cells by a known method (Camu et al., 1993, Purification of spinal motoneurons from chicken and rat embryos by immunopanning. In "Immunoselection Strategies for Neural cell culture", Neuroprotocols: A companion to Methods in Neurosciences 2, 191-199; Henderson et al., 1993, Neutrophins promote motoneuron survival and are present in embryonic limb bud. Nature 363 (6426):266-70).

The cells are centrifuged on a density gradient. The motoneurons are enriched in the fraction of large cells (the most dense). The cells of this fraction are incubated with an anti-p75 antibody, a surface antigen present on motoneurons.

Secondary antibodies coupled to magnetic beads are added and the mixture of cells is passed through a column in a magnet (Arce et al., 1999 Cardiotrophin-1 requires LIFRbeta to promote survival of mouse motoneurons purified by a novel technique. J. Neurosci Res 55(1): 119-26). Only the motoneurons are retained: their purity is of the order of 90%.

The motoneurons are seeded at low density in culture wells on a polyornithine-laminin substrate in a Neurobasal medium (GIBCO) supplemented according to Raoul et al., 1999, Programmed cell death of embryonic motoneurons triggered through the Fas death receptor. J Cell Biol 147(5):1049-62.

Negative controls (absence of trophic factors) and positive controls (in the presence of BDNF (Brain-Derived Neurotrophic Factor) at 1 ng/ml, GDNF (Glial-Derived Neurotrophic Factor) at 1 ng/ml and CNTF (Ciliary Neurotrophic Factor) at 10 ng/ml, marketed by the American company PEPROTECH, Inc. and the company Sigma-Aldrich, are included in each series.

The test compounds are added 60 minutes after seeding and the cultures are kept at 37° C. under 5% $CO_2$ for 3 days.

The motoneurons have a spontaneous tendency to die in the absence of neurotrophic factors (Pettmann and Henderson, 1998, Neuronal cell death. Neuron 20(4):633-47). After 3 days, survival is evaluated by measurement of fluorescence after incubation of the cells in the presence of calcein, which becomes fluorescent in living cells.

After 3 days of culture at 37° C., under 5% $CO_2$ and at saturating humidity, up to 50% of the motoneurons seeded initially survive in the medium supplemented with neurotrophic factors, whereas less than 15% of the motoneurons survive in the culture medium without addition of neurotrophic factors.

The neuroprotective activity of the test compounds was evaluated by their capacity for preventing death of motoneurons when they are added to the Neurobasal medium (GIBCO) in comparison with the survival of motoneurons in the medium to which neurotrophic factors were added.

The compounds of formula I according to the invention showed neuroprotective activity at a concentration capable of giving a better survival rate of the motoneurons in the Neurobasal medium.

This survival rate is expressed by the number of living cells after treatment with the test compound relative to the survival induced by the neurotrophic factors. This ratio can therefore represent the percentage survival due to the compound tested relative to the survival induced by the neurotrophic factors. If the ratio is greater than 0, the compounds have a positive effect on survival of the motoneurons.

The results obtained are as follows:

| Compound No. | Concentration in μM | Ratio |
| --- | --- | --- |
| 2 | 3 | >0.2 |
| 3 | 1 | >0.2 |
| 4 | 0.3 | >0.2 |
| 5 | 1 | >0.2 |
| 6 | 3 | >0.2 |
| 7 | 1 | >0.2 |
| 9 | 1 | >0.2 |
| 8 | 1 | >0.2 |
| 10 | 1 | >0.2 |
| 11 | 1 | >0.2 |
| 12 | 1 | >0.2 |

Based on their trophic effect on the spinal motoneurons, the compounds of formula (I) according to the invention are therefore shown to be potentially useful as a medicament, in particular in the treatment of amyotrophies, in particular in the treatment of amyotrophic lateral sclerosis or of infantile spinal muscular atrophies, and in the treatment of spinal cord injuries.

The invention claimed is:

1. A Compound selected from the group consisting of:
4-nor-3,5-seco-3-(trifluoromethyl)cholestan-3-ol-5-one oxime;
3-[(N-(+)-biotinoyl-N-methyl)amino]-4-nor-3,5-secocholestan-5-one oxime;
3-[methyl(7-nitro-2,1,3-benzoxadiazol-4-yl)amino]-4-nor-3,5-secocholestan-5-one oxime;
25-fluoro-4-nor-3,5-secocholestan-3-ol-5-one oxime;
4-nor-3,5-secocholestan-5-one oxime;
3,4-dinor-2,5-secocholestan-2-ol-5-one oxime;
4-nor-3,5-secocholest-24-en-3-ol-5-one oxime; and
24β-ethyl-4-nor-3,5-secocholest-22-en-3-ol-5-one oxime.

2. A method of treating spinal muscular atrophy, or amyotrophic lateral sclerosis, comprising administering an effective amount of at least one compound according to claim 1 to a subject in need thereof.

3. The method according to claim 2, wherein spinal muscular atrophy is infantile spinal muscular atrophy.

4. A compound selected from the group consisting of
3,3-difluoro-4,5-secocholestan-5-one oxime
4-nor-3,5-secocholestan-3,25-diol-5-one oxime
4-nor-3,5-seco-3-(trifluoromethyl)cholestan-3-ol-5-one oxime
3-[(N-(+)-biotinoyl-N-methyl)amino]-4-nor-3,5-secocholestan-5-one oxime
3-[methyl-(7-nitro-2,1,3-benzoxadiazol-4-yl)amino]-4-nor-3,5-secocholestan-5-one oxime
25-fluoro-4-nor-3,5-secocholestan-3-ol-5-one oxime
4-nor-3,5-secocholestan-5-one oxime
4-nor-3,5-secocholest-6-en-3-ol-5-one oxime, 7-hydroxyamino-4-nor-3,5-secocholest-6-an-3-ol-5-one oxime
3,4-dinor-2,5-secocholestan-2-ol-5-one oxime
4-nor-3,5-secocholest-24-en-3-ol-5-one oxime
24β-ethyl-4-nor-3,5-secocholest-22-en-3-ol-5-one oxime as well as:

its SYN, ANTI isomers, when they exist,
its optical isomers (enantiomers, diastereoisomers), when they exist,
its addition salts with a pharmaceutically acceptable acid or base,
its hydrates and its solvates,
its prodrugs.

5. The compound according to claim 4, characterized in that it is:
3-[(N-(+)-biotinoyl-N-methyl)amino]-4-nor-3,5-secocholestan-5-one oxime or
3-[methyl-(7-nitro-2,1,3-benzoxadiazol-4-yl)amino]-4-nor-3,5-secocholestan-5-one oxime.

6. A method of treating spinal muscular atrophy or amyotrophic lateral sclerosis, comprising administering an effective amount of at least one compound according to claim 4 to a subject in need thereof.

7. The method according to claim 6, wherein spinal muscular atrophy is infantile spinal muscular atrophy.

* * * * *